(12) United States Patent
Hashimoto et al.

(10) Patent No.: US 10,618,882 B2
(45) Date of Patent: Apr. 14, 2020

(54) PYRIDINE-2-YL PYRIDINIUM COMPOUND AND METHOD OF USING SAME

(71) Applicant: Nippon Soda Co., Ltd., Chiyoda-ku, Tokyo (JP)

(72) Inventors: Yuki Hashimoto, Ichihara (JP); Katsumi Okada, Joetsu (JP); Fuminori Komatsu, Takaoka (JP); Satoshi Kajita, Joetsu (JP); Tomomi Kobayashi, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 251 days.

(21) Appl. No.: 15/746,885

(22) PCT Filed: Jul. 26, 2016

(86) PCT No.: PCT/JP2016/071833
§ 371 (c)(1),
(2) Date: Jan. 23, 2018

(87) PCT Pub. No.: WO2017/018409
PCT Pub. Date: Feb. 2, 2017

(65) Prior Publication Data
US 2019/0389833 A1    Dec. 26, 2019

(30) Foreign Application Priority Data
Jul. 28, 2015 (JP) ................................. 2015-149045

(51) Int. Cl.
*C07D 401/04* (2006.01)
*C07D 451/14* (2006.01)

(52) U.S. Cl.
CPC ......... *C07D 401/04* (2013.01); *C07D 451/14* (2013.01)

(58) Field of Classification Search
CPC ............................ C07D 401/04; C07D 451/14
See application file for complete search history.

(56) References Cited

U.S. PATENT DOCUMENTS

| 2012/0289700 A1 | 11/2012 | Hamamoto et al. |
| 2012/0309964 A1 | 12/2012 | Hamamoto et al. |

FOREIGN PATENT DOCUMENTS

| JP | 2011-520778 A | 7/2011 |
| RU | 2 303 599 C1 | 7/2007 |
| WO | WO 01/12604 A1 | 2/2001 |
| WO | WO 2005/025315 A1 | 3/2005 |
| WO | WO 2009/115557 A2 | 9/2009 |
| WO | WO 2011/078081 A1 | 6/2011 |
| WO | WO 2011/105506 A1 | 9/2011 |

OTHER PUBLICATIONS

Owen et al., Pyridinium-Derived N-Heterocyclic Carbene Complexes of Platinum: Synthesis, Structure and Ligand Substitution Kinetics, 126 J. Am Chem. Soc. 8247-8255 (2004) (Year: 2004).*

Extended European Search Report dated Feb. 13, 2019, PCT/JP2016/071833.
Boduszek et al., "A New Method for the Preparation of Pyridine-4-phosphonic Acids", SYTHESIS, Georg Thieme Verlag, Stuttgart, DE, Jun. 1979 (Jun. 1979), pp. 452-453, XP002639180, ISSN: 0039-7881.
Katritzky et al., "Nucleophilic Displacements of N-Aryl and Heteroaryl Groups. Part 4. Pyrylium-mediated Transformations of Heteroarylamines into Pyridinium Salts and their Inter- and Intra-molecular Displacement", Journal of the Chemical Society, Perkin Transactions 1, Jan. 1983 (Jan. 1983), pp. 2617-2621, XP055527957, DOI: 10.1039/P19830002617.
Hamana et al., "Studies on Tertiary Amine Oxides. XII. Reactions of Pyridine 1-Oxides with Tosyl Chloride in the Presence of Pyridine", Yakugaku Zasshi, Journal of the Pharmaceutical Society of Japan, vol. 82, No. 4, Jan. 1962 10.1248/yakushi1947.82.4_518.
Begunov et al., "Effect of Hydrochloric Acid on the Reductive Animation of 1-(3-Nitropyridin-2-yl)pyridinium Salts", Russian Journal of Organic Chemistry, vol. 43, No. 7, July (Jul. 2007), pp. 1098-1100, XP055527864, US ISSN: 1070-4280, DOI: 10.1134/s1070428007070287.
Boduszek et al., "Synthesis of Dipyridyl Sulfides from Pyridyl-Pyridinium Halides", Monatshefte fur Chemie, Chemical Monthly, vol. 111, No. 5, Jan. 1980 (Jan. 1980), pp. 1111-1116, XP055527963, Vienna ISSN: 0026-9247, DOI: 10.1007/BF00909667.
International Search Report dated Oct. 11, 2016, in PCT/JP2016/071833.
Begunov et al., "Synthesis of pyrido[3',2':4,5]imidazo[1,2-α]pyridines by reductive cyclisation of pyridinium salts," Mendeleev Communications, 2006, 16(2):119-120.
Hamana et al., "Studies on tertiary amine oxides. XX. Reactions of pyridine 1-oxide derivatives with tosyl chloride in the presence of pyridine," Journal of Pharmaceutical Society of Japan, 1964, 84:23-27.
Owen et al., "Pyridinium-Derived N-Heterocyclic Carbene Complexes of Platinum: Synthesis, Structure and Ligand Substitution Kinetics," Journal of the American Chemical Society, Aug. 12, 2004, 126(26):8247-8255.
Picek et al., "Tandem β-Elimination/Hetero-Michael Addition Rearrangement of an N-Alkylated Pyridinium Oxime to an O-Alkylated Pyridine Oxime Ether: An Experimental and Computational Study," The Journal of Organic Chemistry, Jan. 6, 2015, 80(4):2165-2173.

(Continued)

*Primary Examiner* — Timothy R Rozof
(74) *Attorney, Agent, or Firm* — Foley & Lardner LLP

(57) ABSTRACT

A compound represented by formula (I), wherein $A^-$ represents a halogen ion, a benzenesulfonate ion, an alkylsulfonate ion or the like, X represents a halogeno group or the like, a is an integer of 0 to 4, Y represents a C1-C8 alkyl group or the like, b is an integer of 0 to 5.

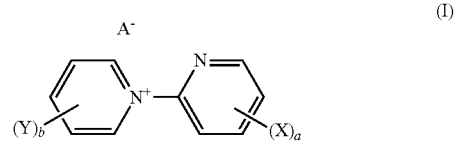

(I)

3 Claims, No Drawings

(56) References Cited

OTHER PUBLICATIONS

Wibaut et al., "The formulation of N-pyridylpyridinium compounds from monohalogenated pyridines," Bulletin de la Societe Chimique de France, 1958, 424-428.
Yakolev et al., "ω-Substituted-2-(polyenamino)- or Annelated Nitropyridines from 1-(3-Cyano-5-nitropyridyl-2)-pyridinium Salts," Tetrahedron, 1998, 54:5775-5780.
Zalewski et al,. "Studies on the Quantitative Determination of Pyridine in Coal Tars. I. The Alkaline Hydrolysis of the Products of the Reactions of Some Chloronitrocompounds with Pyridine," Chemia Analityczna, 1976, 21(1):73-83.
Zalewski et al., "Studies on the Quantitative Determination of Pyridine Bases in Coal Tars. II. Reactions of Chloro-2,4-dinitrobenzene and 2-Chloro-5-Nitropyridine with Methylpyridines," Chemia Analityczna, 1976, 21(6):1275-1281.
Office Action dated Sep. 13, 2019, in Indian Patent Application No. 201847002530, including English translation.
Extended European Search Report dated Feb. 13, 2019, in European Application No. 16830514.2.

* cited by examiner

PYRIDINE-2-YL PYRIDINIUM COMPOUND AND METHOD OF USING SAME

TECHNICAL FIELD

The present invention relates to a pyridine-2-yl pyridinium compound useful as an intermediate for producing a pyridine-2-yl oxyamine compound having insecticidal and acaricidal activity, and a method of using the same.

This application is a National Stage application of PCT/JP2016/071833, filed Jul. 26, 2016, which claims priority from Japanese Patent Application No. 2015-149045, filed Jul. 28, 2015, the content of which is incorporated herein by reference.

BACKGROUND ART

As a compound having excellent insecticidal and acaricidal activity, an N-(pyridine-2-yloxy)-amine compound such as 3-endo-[2-i-butoxy-4-(trifluoromethyl) phenoxy]-9-[5-(trifluoromethyl)-2-pyridyloxy]-9-azabicyclo [3,3,1] nonane (refer to formula (H-1)) have been proposed (Patent Document 1).

[Chemical formula 1]

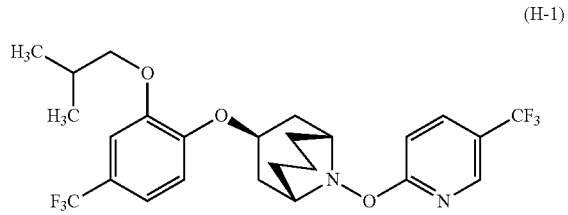

(H-1)

According to Patent Document 1, the compound represented by formula (H-1) can be prepared with a yield of 80% or more by, for example, reacting 3-endo-[2-i-butoxy-4-(trifluoromethyl) phenoxy]-9-hydroxy-9-azabicyclo [3,3,1] nonane with 2-chloro-5-(trifluoromethyl) pyridine at a low temperature of −20 to 0° C. in the presence of a base (refer to formula (A)).

[Chemical formula 2]

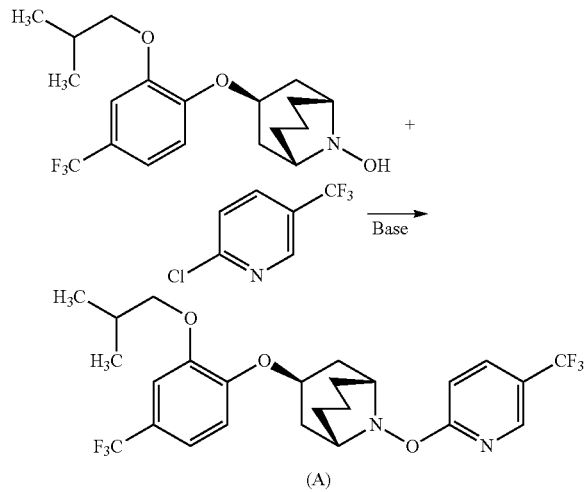

(A)

PRIOR ART LITERATURE

Patent Documents

Patent document 1: WO2011/105506 A1

Non-Patent Document

Non-patent document 1: Jonatahn S. Owen et al. "Pyridiniumu-Derived N-Heterocyclic Carbene Complexes of Platinum: Synthesis, Structure and Ligand Substitution Kinetics" J. AM. Chem. Soc. 2004, 126 8247-8255

DISCLOSURE OF INVENTION

Problems to be Solved by the Invention

However, when this reaction is carried out at a temperature around room temperature, the reaction becomes unstable and the yield is significantly lowered.

The objective of the present invention is to provide a pyridine-2-ylpyridinium compound which enables to produce pyridine-2-yloxyamine compounds having excellent acaricidal activity and excellent safety with a high yield by stably reacting at a temperature around room temperature, and a method of using the same.

Means for Solving the Problems

As a result of intensive studies to solve the above problems, the present inventors have completed the present invention including the following aspects.

[1] A compound represented by formula (I).

[Chemical formula 3]

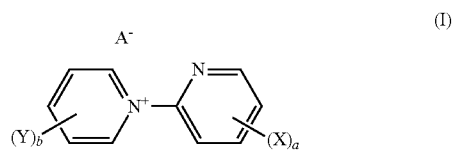

(I)

In formula (I), A⁻ represents a halogen ion, an unsubstituted or substituted benzenesulfonate ion, or an unsubstituted or substituted C1-C8 alkylsulfonate ion (excluding trifluoromethane sulfonate ion).

X represents a halogeno group, an unsubstituted or substituted C1-C8 alkyl group, an unsubstituted or substituted C1-C8 alkylsulfonyl group, a nitro group, a cyano group, an unsubstituted or substituted C1-C6 alkoxycarbonyl group, or an unsubstituted or substituted phenyl group. a is an integer of 0 to 4. When a is 2 or more, X may be the same or different.

Y represents an unsubstituted or substituted C1-C8 alkyl group, an unsubstituted or substituted C1-C8 alkoxy group, or an unsubstituted or substituted C1-C8 dialkylamino group. b is an integer of 0 to 5. When b is 2 or more, Y may be the same or different.

[2] The compound according to [1], wherein
b is 1,
Y is a group represented by NR¹R² substituting at the 4-position,
R¹ and R² each independently represent an unsubstituted or substituted C1-C8 alkyl group, and $R^1$ and $R^2$ may bond together to form a ring containing a nitrogen atom to which they are bonded as a constituting atom of the ring.

[3] The compound according to [2], wherein $A^-$ is a chlorine ion, and $R^1$ and $R^2$ are methyl groups.

[4] The compound according to any one of [1], [2] and [3], wherein

X is $C_nZ_pF_{2n+1-p}$, a is an integer of 1 to 4, and when a is 2 or more, $C_nZ_pF_{2n+1}-p$ may be the same or different.

n is an integer from 1 to 6, p is an integer from 0 to 9,

Z represents a hydrogen atom or a halogen atom.

[5] The compound according to any one of [1], [2] and [3], wherein a is 1, and X is $CF_3$ substituting at the 5-position.

[6] A method for producing a compound represented by formula (V), including reacting the compound defined in any one of [1] to [5] with a compound represented by formula (IV).

[Chemical formula 4]

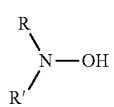

(IV)

[Chemical formula 5]

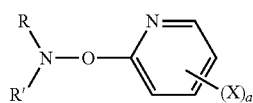

(V)

(in formula (IV) and (V),

R and R' each independently represent an unsubstituted or substituted C1-C8 alkyl group, an unsubstituted or substituted C2-C8 alkenyl group, an unsubstituted or substituted C2-C8 alkynyl Group, an unsubstituted or substituted phenyl group, or an unsubstituted or substituted heterocyclic group. R and R' may bond together to form a ring containing a nitrogen atom to which they are bonded as a constituting atom.

in formula (V), X and a are as defined in [1], [2], [3] or [4].)

[7] The method according to [6], wherein the ring formed by R, R' and the nitrogen atom to which they are bonded is a 5- to 8-membered monocyclic ring.

[8] The method according to [6], wherein the ring formed by R, R' and the nitrogen atom to which they are bonded is a monocyclic ring having at least 1 nitrogen atom and at most 7 carbon atoms as ring-constituting atoms that are 5 to 8 in total, the monocyclic ring may have, as substituent $R^a$, an unsubstituted or substituted C1-C8 alkyl group, an unsubstituted or substituted C2-C8 alkenyl group, an unsubstituted or substituted C2-C8 alkynyl group, a hydroxyl group, an unsubstituted or substituted C1-C8 alkoxy group, an unsubstituted or substituted C2-C8 alkenyloxy group, an unsubstituted or substituted C2-C8 alkynyloxy group, an unsubstituted or substituted C1-C7 acyl group, an unsubstituted or substituted C1-C7 acyloxy group, an unsubstituted or substituted phenyl group, an unsubstituted or substituted phenoxy group, an unsubstituted or substituted heterocyclic group, an unsubstituted or substituted heterocyclic oxy group, a halogeno group, or a cyano group, when there are plural substituents $R^a$, substituents $R^a$ may be the same or different, and the plural substituents $R^a$ may bond together to form an oxo group or a ring containing carbon atoms to which the substituents $R^a$ are bonded as ring-constituting atoms.

[9] The method according to [7] or [8], wherein the monocyclic ring is a 6-membered ring containing 1 nitrogen atom and 5 carbon atoms as a ring-constituting atom.

[10] The method according to [6], wherein the ring formed by R, R' and the nitrogen atom to which they are bonded is a 7- to 9-membered bridged ring.

[11] The method according to [6], wherein the ring formed by R, R' and the nitrogen atom to which they are bonded is a bridged ring containing at least 1 nitrogen atom and at most 8 carbon atoms as ring-constituting atoms that are 7 to 9 in total, the bridged ring may have, as substituent $R^a$, an unsubstituted or substituted C1-C8 alkyl group, an unsubstituted or substituted C2-C8 alkenyl group, an unsubstituted or substituted C2-C8 alkynyl group, a hydroxyl group, an unsubstituted or substituted C1-C8 alkoxy group, an unsubstituted or substituted C2-C8 alkenyloxy group, an unsubstituted or substituted C2-C8 alkynyloxy group, an unsubstituted or substituted C1-C7 acyl group, an unsubstituted or substituted C1-C7 acyloxy group, an unsubstituted or substituted phenyl group, an unsubstituted or substituted phenoxy group, an unsubstituted or substituted heterocyclic group, an unsubstituted or substituted heterocyclic oxy group, a halogeno group, or a cyano group, when there are plural substituents $R^a$, they may be the same or different, and the plural substituents $R^a$ may bond together to form an oxo group or a ring containing carbon atoms to which the substituents $R^a$ are bonded as ring-constituting atoms.

[12] the method according to [10] or [11], wherein the bridged ring composed of a 6-membered ring containing 1 nitrogen atom and 5 carbon atoms as a ring-constituting atom, and a bridge portion containing 1 to 3 carbon atoms which bridges between two non-adjacent carbon atoms constituting the 6-membered ring.

[13] The method according to [11], wherein the bridged ring is represented by formula (VI).

[Chemical formula 6]

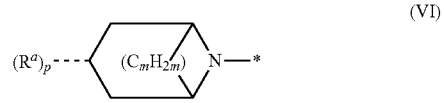

(VI)

(in formula (VI), m is an integer of 1 to 3, p is an integer of 0 to 2, when p is 1, the bond represented by broken line represents a single bond, when p is 2, the bond represented by broken line represents two single bonds or one double bond, two $R^a$ bonded to the ring by single bonds may be the same or different, $R^a$ bonded to the ring by a double bond is an oxo group,

* represents a bonding position.

Effects of the Invention

The pyridine-2-ylpyridinium compound according to the present invention is useful as, for example, an intermediate for producing a pyridine-2-yloxyamine compound.

By reacting the pyridine-2-ylpyridinium compound according to the present invention with a hydroxylamine compound, a pyridine-2-yloxyamine compound can be obtained with a high yield. Since this reaction can be carried out stably even at a temperature around room temperature, the production cost of the pyridine-2-yloxyamine compound can be lowered.

BEST MODE FOR CARRYING OUT THE INVENTION

The pyridine-2-ylpyridinium compound according to the present invention is a compound represented by formula (I).

First, the meanings of "unsubstituted" and "substituted" in this specification will be explained.

The term "unsubstituted" means that the specified group is solely formed of a group serving as a mother nucleus. When only the name of the group serving as the mother nucleus is mentioned without mention of "substituted", it means "unsubstituted" unless otherwise stated.

On the other hand, the term "substituted" means that a hydrogen atom of a group serving as a mother nucleus has been substituted with a substituent having the same or a different structure from the mother nucleus. The "substituent" may be one or two or more. The two or more substituents may be the same or different.

The term "C1-C6" or the like indicates that the number of carbon atoms in the group serving as a mother nucleus is 1 to 6. This number of carbon atoms does not include the number of carbon atoms present in the substituent. For example, a butyl group having an ethoxy group as a substituent is classified as a C2 alkoxy C4 alkyl group.

The "substituent" is not particularly limited as long as it is chemically acceptable and it has the effects of the present invention.

Examples of the substituent include a halogeno group such as a fluoro group, chloro group, bromo group, iodo group or the like;

a C1-C6 alkyl group such as a methyl group, ethyl group, n-propyl group, i-propyl group, n-butyl group, s-butyl group, i-butyl group, t-butyl group, n-pentyl group, n-hexyl group or the like.

a C3-C8 cycloalkyl group such as a cyclopropyl group, cyclobutyl group, cyclopentyl group, cyclohexyl group, cycloheptyl group or the like;

a C2-C6 alkenyl group such as a vinyl group, 1-propenyl group, 2-propenyl group (allyl group), 1-butenyl group, 2-butenyl group, 3-butenyl group, 1-methyl-2-propenyl group, 2-methyl-2-propenyl group or the like;

a C4-C8 cycloalkenyl group such as a 2-cyclopentenyl group, 3-cyclohexenyl group, 4-cyclooctenyl group or the like;

a C2-C6 alkynyl group such as an ethynyl group, 1-propynyl group, 2-propynyl group, 1-butynyl group, 2-butynyl group, 3-butynyl group, 1-methyl-2-propynyl group or the like;

a C1-C6 alkoxy group such as a methoxy group, ethoxy group, n-propoxy group, i-propoxy group, n-butoxy group, s-butoxy group, i-butoxy group, t-butoxy group or the like;

a C2-C6 alkenyloxy groups such as a vinyloxy group, allyloxy group, propenyloxy group, butenyloxy group or the like;

a C2-C6 alkynyloxy group such as an ethynyloxy group, propargyloxy group or the like;

a C6-C10 aryl group such as a phenyl group, naphthyl group or the like;

a C6-C10 aryloxy group such as a phenoxy group, 1-naphthoxy group or the like;

a C7-C11 aralkyl group such as a benzyl group, phenethyl group or the like;

a C7-C11 aralkyloxy groups such as a benzyloxy group, phenethyloxy group or the like;

a C1-C7 acyl group such as a formyl group, acetyl group, propionyl group, benzoyl group, cyclohexylcarbonyl group or the like;

a C1-C7 acyloxy group such as a formyloxy group, acetyloxy group, propionyloxy group, benzoyloxy group, cyclohexylcarbonyloxy group or the like;

a C1-C6 alkoxycarbonyl group such as a methoxycarbonyl group, ethoxycarbonyl group, n-propoxycarbonyl group, i-propoxycarbonyl group, n-butoxycarbonyl group, t-butoxycarbonyl group or the like;

a carboxyl group:

a hydroxyl group;

a halo C1-C6 alkyl group such as a chloromethyl group, chloroethyl group, trifluoromethyl group, 1,2-dichloro-n-propyl group, 1-fluoro-n-butyl group, perfluoro-n-pentyl group or the like;

a halo C2-C6 alkenyl group such as a 2-chloro-1-propenyl group, 2-fluoro-1-butenyl group or the like;

a halo C2-C6 alkynyl group such as a 4,4-dichloro-1-butynyl group, 4-fluoro-1-pentynyl group, 5-bromo-2-pentynyl group or the like;

a halo C1-C6 alkoxy groups such as a trifluoromethoxy group, 2-chloro-n-propoxy group, 2,3-dichlorobutoxy group or the like;

a halo C2-C6 alkenyloxy group such as a 2-chloropropenyloxy group, 3-bromobutenyloxy group or the like;

a halo C6-C10 aryl group such as a 4-chlorophenyl group, 4-fluorophenyl group, 2,4-dichlorophenyl group or the like;

a halo C6-C10 aryloxy group such as a 4-fluorophenyloxy group, 4-chloro-1-naphthoxy group or the like;

a halogen-substituted C1-C7 acyl groups such as a chloroacetyl group, trifluoroacetyl group, trichloroacetyl group, 4-chlorobenzoyl group or the like;

a cyano group; a nitro group; an amino group;

a C1-C6 alkylamino group such as a methylamino group, dimethylamino group, diethylamino group or the like;

a C6-C10 arylamino group such as an anilino group, naphthylamino group or the like;

a C7-C11 aralkylamino group such as a benzylamino group, phenethylamino group or the like;

a C1-C7 acylamino groups such as a formylamino group, acetylamino group, propanoylamino group, butyrylamino group, i-propylcarbonylamino group, benzoylamino group or the like;

a C1-C6 alkoxycarbonylamino group such as a methoxycarbonylamino group, an ethoxycarbonylamino group, n-propoxycarbonylamino group, i-propoxycarbonylamino group or the like;

an unsubstituted or substituted aminocarbonyl group such as an aminocarbonyl group, dimethylaminocarbonyl group, phenylaminocarbonyl group, N-phenyl-N-methylaminocarbonyl group or the like;

an imino group-substituted C1-C6 alkyl group such as an iminomethyl group, (1-imino) ethyl group, (1-imino)-n-propyl group or the like;

an unsubstituted or substituted hydroxyimino group-substituted C1-C6 alkyl group such as a hydroxyiminomethyl group, (1-hydroxyimino) ethyl group, (1-hydroxyimino) propyl group, methoxyiminomethyl group, (1-methoxyimino) ethyl group or the like;

a mercapto group;

a C1-C6 alkylthio group such as a methylthio group, ethylthio group, n-propylthio group, i-propylthio group, n-butylthio group, i-butylthio group, s-butylthio group, t-butylthio group or the like;

a C6-C10 arylthio group such as a phenylthio group, naphthylthio group or the like;

a heteroarylthio group such as a thiazolylthio group, pyridylthio group or the like;

a C7-C11 aralkylthio group such as a benzylthio group, phenethylthio group or the like;

a C1-C6 alkylsulfonyl group such as a methylsulfonyl group, ethylsulfonyl group, t-butylsulfonyl group or the like;

a C6-C10 arylsulfonyl group such as a phenylsulfonyl group or the like;

a heteroarylsulfonyl group such as a thiazolylsulfonyl group, pyridylsulfonyl group or the like;

a C7-C11 aralkylsulfonyl group such as a benzylsulfonyl group, phenethylsulfonyl group or the like;

a 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

a 6-membered heteroaryl group such as a pyridyl group, pyrazinyl group, pyrimidinyl group, pyridanidyl group, triazinyl group or the like;

a saturated heterocyclic group such as an aziridinyl group, epoxy group, pyrrolidinyl group, tetrahydrofuranyl group, piperidyl group, piperazinyl group, morpholinyl group or the like;

a tri C1-C6 alkyl-substituted silyl group such as a trimethylsilyl group, triethylsilyl group, t-butyldimethylsilyl group or the like;

a triaryl-substituted silyl group such as a triphenylsilyl group or the like; and the like.

In addition, it is acceptable that at least one hydrogen atom among these "substituents" is substituted with a group having the same or different structure. For example, those in which a hydrogen atom in an alkyl group is substituted with an alkoxy group, namely, an alkoxyalkyl group or the like, can be mentioned.

[A$^-$]

A$^-$ in formula (I) represents a halogen ion, an unsubstituted or substituted benzenesulfonate ion, or an unsubstituted or substituted C1-C8 alkylsulfonate ion (excluding trifluoromethanesulfonate ion).

Examples of the halogen ion include a fluoride ion, chlorine ion, bromine ion, and iodide ion.

Examples of the unsubstituted or substituted benzenesulfonate ion include a p-methylphenylsulfonate ion, p-trifluoromethylphenylsulfonate ion, dodecylbenzenesulfonate acid ion, and the like.

Examples of the unsubstituted or substituted C1-C8 alkylsulfonate ion include a methylsulfonate ion, trifluoromethylsulfonate ion, and the like.

Among these examples, A$^-$ is preferably a halogen ion. Among the halogen ions, a chlorine ion and fluoride ion are preferable, and a chlorine ion is more preferable.

[Y]

Y in formula (I) represents an unsubstituted or substituted C1-C8 alkyl group, an unsubstituted or substituted C1-C8 alkoxy group, or an unsubstituted or substituted di C1-C8 alkylamino group. b is an integer of 0 to 5. When b is 2 or more. Y may be the same or different.

Examples of the C1-C8 alkyl group include a methyl group, ethyl group, n-propyl group, n-butyl group, n-pentyl group, n-hexyl group, n-heptyl group, n-octyl group, i-propyl group, i-butyl group, s-butyl group, t-butyl group, i-pentyl group, neopentyl group, 2-methylbutyl group, 2,2-dimethylpropyl group, i-hexyl group and the like. Among these examples, a C1-C6 alkyl group is preferable.

Examples of the substituted C1-C8 include a cycloalkylalkyl group such as a cyclopropylmethyl group, 2-cyclopropylethyl group, cyclopentylmethyl group, 2-cyclohexylethyl group or the like, preferably a C3-C6 cycloalkyl C1-C6 alkyl group; a cycloalkenylalkyl group such as a cyclopentenylmethyl group, 3-cyclopentenylmethyl group, 3-cyclohexenylmethyl group, 2-(3-cyclohexenyl) ethyl group or the like, preferably a C4-C6 cycloalkenyl C1-C6 alkyl group;

a haloalkyl group such as a fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group, perfluorooctyl group, perchlorooctyl group, 2,4,6-trichlorohexyl group, perfluorodecyl group, 2, 2, 4, 4, 6, 6-hexachlorooctyl group or the like, preferably a C1-C6 haloalkyl group;

an arylalkyl group (aralkyl group) such as a benzyl group, phenethyl group, 3-phenylpropyl group, 1-naphthylmethyl group, 2-naphthylmethyl group or the like, preferably a C6-10 aryl C1-C6 alkyl group;

a heteroarylalkyl group such as a 2-pyridylmethyl group, 3-pyridylmethyl group, 4-pyridylmethyl group, 2-(2-pyridyl) ethyl group, 2-(3-pyridyl) ethyl group, 2-(4-pyridyl) ethyl group, 3-(2-pyridyl) propyl group, 3-(3-pyridyl) propyl group, 3-(4-pyridyl) propyl group, 2-pyrazinylmethyl group, 3-pyrazinylmethyl group, 2-(2-pyrazinyl) ethyl group, 2-(3-pyrazinyl) ethyl group, 3-(2-pyrazinyl) propyl group, 3-(3-pyrazinyl) propyl group, 2-pyrimidylmethyl group, 4-pyrimidylmethyl group, 2-(2-pyrimidyl) ethyl group, 2-(4-pyrimidyl) ethyl group, 3-(2-pyrimidyl) propyl group, 3-(4-pyrimidyl) propyl group, 2-furylmethyl group, 3-furylmethyl group, 2-(2-furyl) ethyl group, 2-(3-furyl) ethyl group, 3-(2-furyl) propyl group, 3-(3-furyl) propyl group or the like, preferably a 5- to 6-membered heteroaryl C1-C6 alkyl group;

a hydroxyalkyl group such as a hydroxymethyl group, 1-hydroxyethyl group, 2-hydroxyethyl group, 1-hydroxypropyl group, 3-hydroxypropyl group, 1-hydroxy-1-methylethyl group, 2-hydroxy-1,1-dimethylethyl group, 2-hydroxy-1,1-dimethylpropyl group, 2-hydroxy-2-methylpropyl group or the like, preferably a hydroxy C1-C6 alkyl group;

an alkoxyalkyl group such as a methoxymethyl group, ethoxymethyl group, 2-methoxyethyl group, 2-ethoxyethyl group, methoxy n-propyl group, n-propoxymethyl group, i-propoxyethyl group, s-butoxymethyl group, t-butoxyethyl group, 2,2-dimethoxyethyl group, 2,2-dimethoxy-1,1-dimethylethyl group or the like, preferably a C1-C6 alkoxy C1-C6 alkyl group;

an acyloxyalkyl group such as a formyloxymethyl group, acetoxymethyl group, 2-acetoxyethyl group, propionyloxymethyl group, propionyloxyethyl group, preferably a C1-C7 acyloxy C1-C6 alkyl group;

an acylalkyl group such as a formylmethyl group, 2-formylethyl group, 3-formylpropyl group, 1-formyl-1-methylethyl group, 2-formyl-1,1-dimethylethyl group, acetylmethyl group, 2-acetylethyl group, 3-acetylpropyl group, 1-acetyl-1-methylethyl group, 2-acetyl-1, 1-dimethylethyl group, preferably a C1-C7 acyl C1-C6 alkyl group;

an acylalkyl group such as an acetylmethyl group, 2-acetyl ethyl group, 3-acetylpropyl group, 1-acetyl-1-methylethyl group, 2-acetyl-1,1-dimethylethyl group, preferably C1-C7 acyl C1-C6 alkyl group;

a carboxyalkyl group such as a carboxymethyl group, 2-carboxyethyl group, 3-carboxypropyl group, 1-carboxy-1-methylethyl group, 2-carboxy-1,1-dimethylethyl group, preferably a carboxy C1-C6 alkyl group;

an alkoxycarbonylalkyl group such as a methoxycarbonylmethyl group, 2-methoxycarbonylethyl group, 3-methoxycarbonylpropyl group, 1-methoxycarbonyl-1-methylethyl group, 2-methoxycarbonyl-1,1-dimethylethyl group, preferably a C1-C6 alkoxycarbonyl C1-C6 alkyl group; and the like.

Examples of the unsubstituted or substituted C1-C8 alkoxy group include a methoxy group, ethoxy group, n-propoxy group, n-butoxy group, n-pentyloxy group, n-hexyloxy group, i-propoxy group, i-butoxy group, s-butoxy group, t-butoxy group, 1-ethylpropoxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group, 2-ethylbutoxy group, n-pentyloxy group, i-pentyloxy group, 2-methylbutoxy group, n-hexyloxy group: a cycloalkylalkoxy group such as a cyclopropylmethoxy group or the like, a cycloalkenylalkyloxy group such as a cyclopentenylmethoxy group or the like, a haloalkyloxy group such as a fluoromethoxy group or the like, an aralkyloxy group such as a benzyloxy group or the like, a heteroarylalkyloxy group such as a 2-pyridylmethoxy group or the like, a hydroxyalkyloxy group such as a hydroxymethoxy group or the like; and the like.

Examples of the unsubstituted or substituted di C1-C8 alkylamino group include a dimethylamino group, diethylamino group, methylethylamino group, methylpropylamino group, i-propylethylamino group and the like.

In the present invention, it is most preferable that b is 1, and Y is a group represented by $NR^1R^2$ substituting at the 4-position. In the case where Y is a group represented by $NR^1R^2$ substituting at the 4-position, $R^1$ and $R^2$ may each independently represent an unsubstituted or substituted C1-C8 alkyl group, and preferably represent a methyl group, ethyl group, or n-propyl group, and more preferably represent a methyl group. In addition, $R^1$ and $R^2$ may bond together to form a ring containing a nitrogen atom to which they are bonded as a constituting atom of the ring, and in this case, the group represented by $NR^1R^2$ is preferably a pyrrolidinyl group, piperidinyl group or pyrrolinyl group, and more preferably a pyrrolidinyl group.

The compound wherein b is 1, and Y is a group represented by $NR^1R^2$ substituting at the 4-position is a compound represented by formula (II).

[X]

X in formula (I) represents a halogeno group, an unsubstituted or substituted C1-C8 alkyl group, an unsubstituted or substituted C1-C8 alkylsulfonyl group, a nitro group, a cyano group, an unsubstituted or substituted C1-C6 alkoxycarbonyl group, or an unsubstituted or substituted phenyl group. a is an integer of 0 to 4. When a is 2 or more, X may be the same or different.

Examples of the halogeno group include a fluoro group, chloro group, bromo group, iodo group.

Examples of the unsubstituted or substituted C1-C8 alkyl group for X include the same groups as those exemplified for Y.

Examples of the C1-C8 alkylsulfonyl group include a methylsulfonyl group, ethylsulfonyl group, n-propylsulfonyl group, isopropylsulfonyl group, n-butylsulfonyl group, isobutylsulfonyl group, s-butylsulfonyl group, t-butylsulfonyl group, n-pentylsulfonyl group, isopentylsulfonyl group, neopentylsulfonyl group, 1-ethylpropylsulfonyl group, n-hexylsulfonyl group, isohexylsulfonyl group and the like.

Examples of the substituted C1-C8 alkylsulfonyl group include a fluoromethylsulfonyl group, chloromethylsulfonyl group, bromomethylsulfonyl group, difluoromethylsulfonyl group, a dichloromethylsulfonyl group, trifluoromethylsulfonyl group and the like.

Examples of the unsubstituted or substituted C1-C6 alkoxycarbonyl group include a methoxycarbonyl group, ethoxycarbonyl group, isopropoxycarbonyl group, t-butoxycarbonyl group and the like.

Examples of the unsubstituted or substituted phenyl group include a phenyl group, chlorophenyl group, dichlorophenyl group, fluorophenyl group, methylphenyl group, dimethylphenyl group, ethylphenyl group and the like.

Among these examples, X is preferably $C_nZ_pF_{2n+1-p}$, a halogeno group, or a nitro group, and more preferably $C_nZ_pF_{2n+1-p}$. When X is $C_nZ_pF_{2n+1-p}$, a is an integer of 1 to 4, and when a is 2 or more, $C_nZ_pF_{2n+1-p}$ may be the same or different, n is an integer of 1 to 6, p is an integer of 0 to 9, and Z is preferably a hydrogen atom or a halogen atom. a is preferably 1 or 2, and more preferably 1. n is preferably 1. p is preferably 0 or 1, and more preferably 0. Z preferably represents a halogen atom. Examples of the halogen atom include a fluorine atom, chlorine atom, bromine atom and iodine atom, and among these examples, a chlorine atom is preferable.

The pyridine-2-yl group is preferably substituted with $C_nZ_pF_{2n+1-p}$ at the 3, 4, 5 or 6 position, more preferably at the 3, 5 or 6 position, and even more preferably at the 5 position. Examples of $C_nZ_pF_{2n+1-p}$ include $CF_3$, $C_2F_5$, $CHF_2$, $CClF_2$, $CCl_2F$, $CCl_3$, $CBrF_2$ and the like.

The compound wherein X is $C_nZ_pF_{2n+1-p}$ is a compound represented by formula (III). Further, when Y represents the preferable examples described above, the compound is represented by formula (IIIa).

[Chemical formula 7]

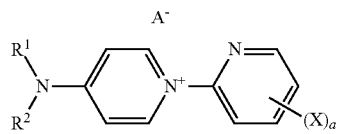

(II)

[Chemical formula 8]

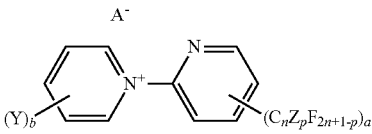

(III)

[Chemical formula 9]

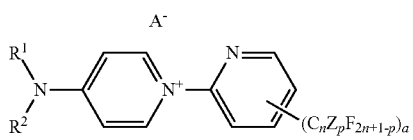
(IIIa)

In the present invention, it is most preferable that a is 1 and X is $CF_3$ substituting at the 5-position.

The compound wherein a is 1 and X is $CF_3$ substituting at the 5-position is a compound represented by formula (IIIb). Further, when Y represents the preferable examples described above, the compound is represented by formula (IIIc).

[Chemical formula 10]

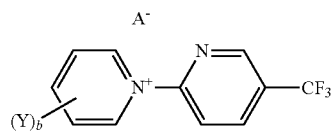
(IIIb)

[Chemical formula 11]

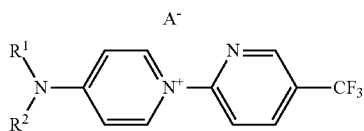
(IIIc)

$R^1$ and $R^2$ in formula (II), formula (IIIa) or formula (IIIc) each independently represent an unsubstituted or substituted C1-C8 alkyl group. Examples of the unsubstituted or substituted C1-C8 alkyl group for $R^1$ and $R^2$ are the same as those exemplified above.

$R^1$ and $R^2$ may bond together to form a ring containing a nitrogen atom to which they are bonded as a constituting atom of the ring. Examples of the ring include 1-azetino, 1-pyrrolidino and the like.

The pyridine-2-yl pyridinium compound according to one embodiment of the present invention can be obtained, for example, by a method including reacting a compound represented by formula (VII) with a compound represented by formula (VIII).

[Chemical formula 12]

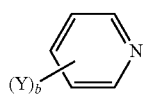
(VII)

[Chemical formula 13]

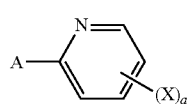
(VIII)

Y and b in formula (VII) are the same as those in formula (I).

X and a in formula (VIII) are the same as those in formula (I).

In formula (VIII), A represents a halogeno group, an unsubstituted or substituted benzenesulfonic acid group, or an unsubstituted or substituted alkylsulfonic acid group (excluding trifluoromethanesulfonic acid group).

Examples of the halogeno group include a fluoro group, chloro group, bromo group, and iodo group.

Examples of the unsubstituted or substituted benzenesulfonic acid group include a p-methylphenylsulfonic acid group, p-trifluoromethylphenylsulfonic acid group, dodecylbenzenesulfonic acid group and the like.

Examples of the unsubstituted or substituted alkylsulfonic acid group include a methylsulfonic acid group, ethylsulfonic acid group, 2,2,2-trifluoroethylsulfonic acid group and the like.

Among these examples, A is preferably a chloro group.

In this reaction, a liquid medium can be used. Examples of the liquid medium include, for example, a tetrahydrofuran, dimethyl ether, dimethylformamide, N-methyl pyrrolidone, dimethylacetamide, toluene, benzene, n-hexane, n-heptane, chloroform, chlorobenzene and the like. These liquid medium can be used alone or in combination of two or more.

The reaction temperature is generally 0-160° C., preferably 60-140° C. Although the reaction time varies depending on the scale of the reaction apparatus, it is generally 1-12 hours.

For example, 1-(4-trifluoromethyl-2-pyridyl)-N, N-dimethyl-4-amino-pyridinium chloride belonging to the pyridine-2-ylpyridinium compound of the present invention can be prepared by reacting 2-chloro-5-trifluoromethylpyridine with N, N-dimethyl-4-aminopyridine (refer to formula (B)).

[Chemical formula 14]

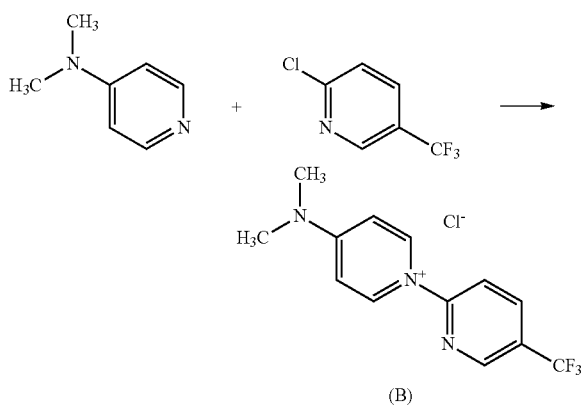
(B)

The pyridine-2-yl pyridinium compound according to one embodiment of the present invention can be suitably used as a raw material for producing a pyridine-2-yloxyamine compound (for example, a compound represented by formula (V)).

[Chemical formula 15]

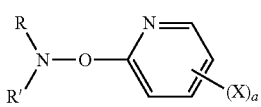
(V)

X and a in formula (V) are the same as those in formula (I).

R and R' in formula (V) each independently represent an unsubstituted or substituted C1-C8 alkyl group, an unsubstituted or substituted C2-C8 alkenyl group, an unsubstituted or substituted C2-C8 alkynyl group, an unsubstituted or substituted phenyl group, or an unsubstituted or substituted heterocyclic group.

Examples of the unsubstituted or substituted C1-C8 alkyl group and the unsubstituted or substituted phenyl group are the same as those exemplified above.

Examples of the C2-C8 alkenyl group include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Examples of the substituted C2-C8 alkenyl group include a haloalkenyl group such as a 2-chloro-1-propenyl group, 2-fluoro-1-butenyl group or the like, and the like.

Examples of the C2-C8 alkynyl group include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Examples of the substituted C2-C8 alkynyl group include a C2-C6 haloalkynyl group such as a 4,4-dichloro-1-butynyl group, 4-fluoro-1-pentynyl group, 5-bromo-2-pentynyl group or the like, and the like.

The heterocyclic group includes at least one hetero atom selected from a nitrogen atom, an oxygen atom and a sulfur atom as a constituting atom of the ring. The heterocyclic group may be monocyclic or polycyclic.

Examples of the heterocyclic group include a 5-membered heteroaryl group, 6-membered heteroaryl group, condensed heteroaryl group, saturated heterocyclic group, partially unsaturated heterocyclic group and the like.

Examples of the 5-membered heteroaryl group include a pyrrolyl group such as a pyrrole-1-yl group, pyrrole-2-yl group, pyrrole-3-yl group or the like; a furyl group such as a furan-2-yl group, furan-3-yl group or the like; a thienyl group such as a thiophen-2-yl group, thiophen-3-yl group or the like; an imidazolyl group such as an imidazol-1-yl group, imidazol-2-yl group, imidazol-4-yl group, imidazol-5-yl group or the like: a pyrazolyl group such as a pyrazol-1-yl group, pyrazol-3-yl group, pyrazol-4-yl group, pyrazol-5-yl group or the like; an oxazolyl group such as an oxazol-2-yl group, oxazol-4-yl group, oxazol-5-yl group or the like; an isoxazolyl group such as an isoxazol-3-yl group, isoxazol-4-yl group, isoxazol-5-yl group or the like; a thiazolyl group such as a thiazol-2-yl group, thiazol-4-yl group, thiazol-5-yl group or the like; an isothiazolyl group such as an isothiazol-3-yl group, isothiazol-4-yl group, isothiazol-5-yl group or the like; a triazolyl group such as 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group or the like; an oxadiazolyl group such as 1,2,4-oxadiazol-3-yl group, 1,2,4-oxadiazol-5-yl group, 1,3,4-oxadiazol-2-yl group or the like; a thiadiazolyl group such as a 1,2,4-thiadiazol-3-yl group, 1,2,4-thiadiazol-5-yl group, 1,3,4-thiadiazol-2-yl group or the like; a tetrazolyl group such as a tetrazol-1-yl group, tetrazol-2-yl group or the like; and the like.

Examples of the 6-membered heteroaryl group include a pyridyl group such as a pyridine-2-yl group, pyridine-3-yl group, pyridine-4-yl group or the like; a pyrazinyl group such as a pyrazin-2-yl group, pyrazin-3-yl group or the like; a pyrimidinyl group such as a pyrimidin-2-yl group, pyrimidin-4-yl group, pyrimidin-5-yl group or the like; a pyridazinyl group such as a pyridazin-3-yl group, pyridazin-4-yl group or the like; a triazinyl group: and the like.

Examples of the condensed heteroaryl group include an indol-1-yl group, indol-2-yl group, indol-3-yl group, indol-4-yl group, indol-5-yl group, indol-6-yl group, indol-7-yl group; a benzofuran-2-yl group, benzofuran-3-yl group, benzofuran-4-yl group, benzofuran-5-yl group, benzofuran-6-yl group, benzofuran-7-yl group; a benzothiophen-2-yl group, benzothiophen-3-yl group, benzothiophen-4-yl group, benzothiophen-5-yl group, benzothiophen-6-yl group, benzothiophen-7-yl group; a benzimidazol-1-yl group, benzimidazol-2-yl group, benzimidazol-4-yl group, benzimidazol-5-yl group, benzoxazol-2-yl group, benzoxazol-4-yl group, benzoxazol-5-yl group, benzothiazol-2-yl group, benzothiazol-4-yl group, benzothiazol-5-yl group; a quinolin-2-yl group, quinolin-3-yl group, quinolin-4-yl group, quinolin-5-yl group, quinolin-6-yl group, quinolin-7-yl group, quinolin-8-yl group; and the like.

Examples of other heterocyclic groups include a 3-membered saturated heterocyclic ring such as an aziridin-1-yl group, aziridin-2-yl group, oxiranyl group or the like; a 5-membered saturated heterocyclic ring such as a pyrrolidin-1-yl group, pyrrolidin-2-yl group, pyrrolidin-3-yl group, tetrahydrofuran-2-yl group, tetrahydrofuran-3-yl group, [1,3] dioxiran-2-yl group or the like; a 6-membered saturated heterocyclic ring such as a piperidin-1-yl group, piperidin-2-yl group, piperidin-3-yl group, piperidin-4-yl group, piperazin-1-yl group, piperazin-2-yl group, morpholin-2-yl group, morpholin-3-yl group, morpholin-4-yl group or the like; a 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group; and the like.

Examples of the substituted heterocyclic group include a 4-chloro-2-pyridinyl group, 3-chloro-2-pyrazinyl group, 4-methyl-2-pyridinyl group, 5-trifluoromethyl-2-pyrimidinyl group, 3-methyl-2-quinolyl group and the like.

R and R' may bond together to form a ring containing a nitrogen atom to which they are bonded as a constituting atom of the ring.

Preferable examples of the ring include a 5- to 8-membered monocyclic ring and 7- to 9-membered bridged ring.

The 5- to 8-membered monocyclic ring is preferably a monocyclic ring containing at least 1 nitrogen atom and at most 7 carbon atoms as ring-constituting atoms that are 5 to 8 in total. The monocyclic ring is preferably a 6-membered ring containing 1 nitrogen atom and 5 carbon atoms as ring-constituting atoms. The 5- to 8-membered ring may be either a saturated monocyclic ring or an unsaturated monocyclic ring.

The 5- to 8-membered monocyclic ring may have, as substituent $R^a$, an unsubstituted or substituted C1-C8 alkyl group, unsubstituted or substituted C2-C8 alkenyl group, unsubstituted or substituted C2-C8 alkynyl group, hydroxyl group, an unsubstituted or substituted C1-C8 alkoxy group, unsubstituted or substituted C2-C8 alkenyloxy group, unsubstituted or substituted C2-C8 alkynyloxy group, unsubstituted or substituted C1-C7 acyl group, unsubstituted or substituted C1-C7 acyloxy group, unsubstituted or substituted phenyl group, unsubstituted or substituted phenoxy group, unsubstituted or substituted heterocyclic group, unsubstituted or substituted heterocyclic oxy group, halogeno group, or cyano group.

When there are plural substituents $R^a$, the substituents $R^a$ may be the same or different. The plurality of $R^a$ may bond together to form an oxo group or a ring containing carbon atoms to which they are bonded as constituting atoms of the ring.

The 7- to 9-membered bridged ring is preferably a bridged ring containing at least 1 nitrogen atom and at most 8 carbon atoms as ring-constituting atoms that are 7 to 9 in total. The 7- to 9-membered bridged ring may be either a saturated bridged ring or an unsaturated bridged ring.

The bridged ring may have, as substituent $R^a$, an unsubstituted or substituted C1-C8 alkyl group, an unsubstituted or substituted C2-C8 alkenyl group, an unsubstituted or substituted C2-C8 alkynyl group, a hydroxyl group, an unsubstituted or substituted C1-C8 alkoxy group, an unsubstituted or substituted C2-C8 alkenyloxy group, an unsubstituted or substituted C2-C8 alkynyloxy group, an unsubstituted or substituted C1-C8 alkylcarbonyloxy group, an unsubstituted or substituted C1-C7 acyl group, an unsubstituted or substituted C1-C7 acyloxy group, an unsubstituted or substituted phenyl group, an unsubstituted or substituted phenoxy group, an unsubstituted or substituted heterocyclic group, an unsubstituted or substituted heterocyclic oxy group, a halogeno group, or a cyano group.

The substituent $R^a$ is preferably an unsubstituted or substituted C1-C8 alkoxy group, an unsubstituted or substituted C2-C8 alkenyloxy group, an unsubstituted or substituted C1-C8 alkylcarbonyloxy group, or an unsubstituted or substituted phenoxy group, and more preferably an unsubstituted or substituted phenoxy group.

When there are plural substituents $R^a$, the substituents $R^a$ may be the same or different. The plurality of $R^a$ may bond together to form an oxo group or a ring containing carbon atoms to which they are bonded as constituting atoms of the ring.

The bridged ring is preferably composed of a 6-membered ring containing 1 nitrogen atom and 5 carbon atoms as ring-constituting atoms, and a bridge portion containing 1 to 3 carbon atoms which bridges between two non-adjacent carbon atoms constituting the 6-membered ring. It is more preferable that the number of carbon atoms in the bridge portion is 3.

It is further preferable that the bridged ring is represented by formula (VI).

[Chemical formula 16]

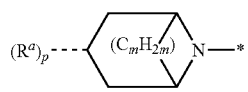

(VI)

(in formula (VI), m is an integer of 1 to 3,
p is an integer from 0 to 2,
when p is 1, the bond represented by broken line indicates a single bond,
when p is 2, the bond represented by broken line indicates two single bonds or one double bond,
two $R^a$ bonded to the ring by single bonds may be the same or different,
$R^a$ bonded to the ring by a double bond is an oxo group,
* represents a bonding position.)

One of the using methods of the pyridine-2-ylpyridinium compound according to one embodiment of the present invention includes a method for producing a pyridine-2-yloxyamine compound (for example, a compound represented by formula (V)). The method for producing a pyridine-2-yloxyamine compound includes reacting a pyridine-2-ylpyridinium compound according to one embodiment of the present invention with a hydroxylamine compound (for example, a compound represented by formula (IV)).

[Chemical formula 17]

(IV)

R and R' in formula (IV) are the same as those in formula (V).

The reaction between the pyridine-2-ylpyridinium compound according to the present invention and the hydroxylamine compound is preferably carried out in the presence of a base.

Examples of the base used in the reaction includes an alkali metal or alkaline earth metal hydroxide such as a lithium hydroxide, sodium hydroxide, potassium hydroxide, cesium hydroxide, magnesium hydroxide; an alkali metal or alkaline earth metal carbonate: an alkali metal or alkaline earth metal hydride: an ammonium salt: an amine salt of an alkali metal: an alkoxide of alkali metal or an alkaline earth metal such as a sodium t-butoxide, sodium methoxide, sodium ethoxide, sodium i-propoxide or the like; an organic amine such as a triethylamine, diisopropylethylamine, diazabicycloundecene, diazabicycloundecene or the like; and the like. These bases can be used alone or in combination of two or more.

In the reaction, a solvent can be used. Examples of the solvent include a tetrahydrofuran, dimethyl ether, dimethylformamide, N-methyl pyrrolidone, dimethylacetamide, toluene, benzene, n-hexane, n-heptane, chloroform, chlorobenzene and the like. These solvents can be used alone or in combination of two or more.

The reaction temperature is preferably −50° C. to 80° C. In the process for producing a cyclic amine of the present invention, even when the reaction is carried out at a temperature around room temperature, the cyclic amine compound (VII) can be obtained with a high yield.

In any of the above-mentioned reactions, it is possible to purify the product after completion of the reaction. Examples of the purification means include a distillation, recrystallization, column chromatography and the like.

The structure of the target product can be identified and confirmed by $^1$H-NMR spectrum, IR spectrum, mass spectrum, elemental analysis and the like.

EXAMPLE

Next, the present invention will be explained in more detail by showing examples. However, the present invention is not limited by these examples. Additions, omissions, substitutions and other changes in the configuration are possible without departing from the scope of the aim of the present invention.

Synthesis of Pyridine-2-ylpyridinium of the Present Invention

Example 1

Synthesis of 1-(5-trifluoromethyl-2-pyridyl)-4-(dimethylamino) pyridinium chloride (I-a)

[Chemical formula 18]

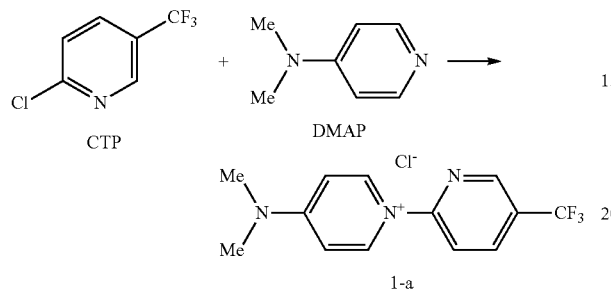

12.2 g (100 mmol) of 4-dimethylaminopyridine and 18.2 g (100 mmol) of 2-chloro-5-(trifluoromethyl) pyridine were dissolved in 30 ml of N, N-dimethylformamide and stirred at 100° C. for 5 hours to obtain a creamy slurry. The slurry was cooled below 20° C. Thereafter, 30 ml of ethyl acetate was added, and a solid material was obtained by suction filtration. 30 ml of ethyl acetate was poured into the solid material and washed. The solid material was dried under vacuum to obtain 29.4 g (yield of 97 mol %) of compound (I-a) which is a pale brown crystal.

Compound (I-a) had a melting point of 274-275° C. and $^1$H-NMR thereof was as follows.

$^1$H-NMR: 3.46 s (6H), 7.33 d (2H), 8.34 d (1H), 8.77 d (1H), 8.94 d (1H), 9.58 d (2H)

Example 2

Synthesis of 1-(5-trifluoromethyl-2-pyridyl)-4-(dimethylamino) pyridinium chloride (I-a)

[Chemical formula 19]

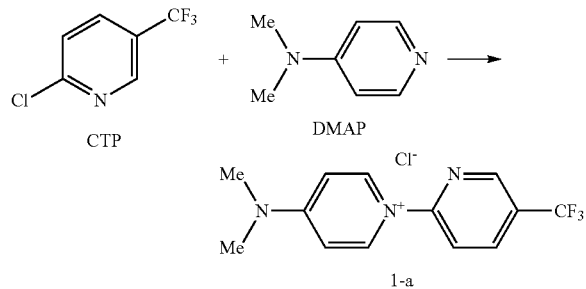

181.54 g (1.00 mol) of 2-chloro-5-(trifluoromethyl) pyridine and 127 g (1.04 mol) of 4-dimethylaminopyridine were dissolved in 230 ml of N, N-dimethylformamide and heated at 120° C. for 3 hours. Thereafter, the resulting solution was cooled to room temperature. Then, 230 ml of toluene was added. A brown-colored suspension was obtained. The suspension was stirred at room temperature for 30 minutes. Thereafter, suction filtration was performed to obtain a solid material. The solid material was washed with 150 ml of toluene and then dried under reduced pressure to obtain 294.6 g (yield of 97 mol %) of compound (I-a) which is a pale brown crystal.

Example 3

Synthesis of 1-(5-chlorodifluoromethyl-2-pyridyl)-4-(dimethylamino) pyridinium chloride (I-b)

[Chemical formula 20]

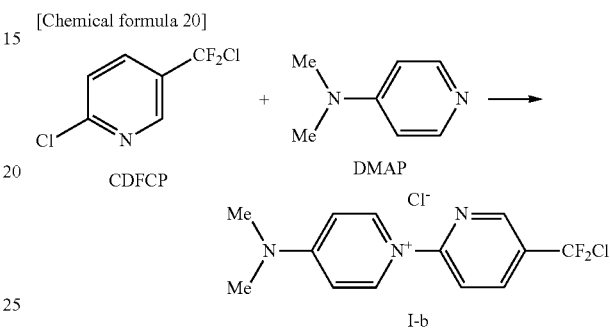

0.49 g (2.47 mmol) of 2-chloro-5(chlorodifluoromethyl) pyridine and 0.32 g (2.62 mmol) of 4-dimethylaminopyridine were dissolved in 2 ml of dry N, N-dimethylformamide and heated at 120-130° C. for 6 hours under a nitrogen atmosphere. Thereafter, the resulting liquid was cooled to 30° C. Then, 15 ml of toluene was poured into the resulting liquid and stirred at 20 to 30° C. for 1 hour. The precipitated solid material was separated by filtration, and the solid material was washed with 5 ml of toluene and dried under vacuum to obtain 0.72 g (91%) of compound (I-b) which is a pale brown crystalline powder.

Compound (I-b) had a melting point of 232 to 234° C. and $^1$H-NMR thereof was as follows.

$^1$H-NMR: 3.47s (6H), 7.30d (2H), 8.34dd (1H), 8.77d (1H), 8.96d (2H), 9.60d (2H)

Example 4

Synthesis of 4-(dimethylamino)-1-(6-trifluoromethyl-2-pyridyl) pyridinium fluoride (I-c)

[Chemical formula 21]

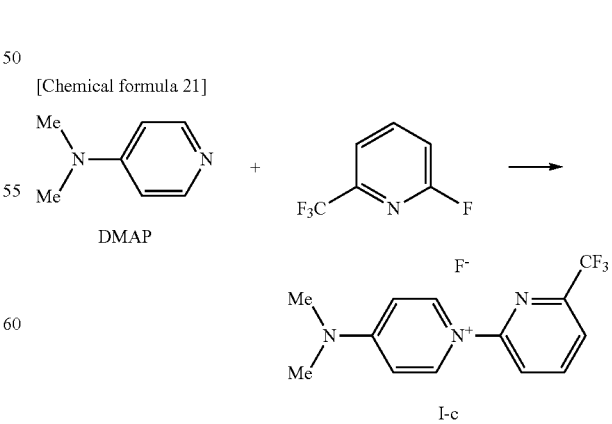

1.01 g (6.11 mmol) of 2-fluoro-6-(trifluoromethyl) pyridine and 0.75 g (6.14 mmol) of 4-dimethylaminopyridine were dissolved in 4 ml of N, N-dimethylformamide and heated at 120° C. for 5 hours. Thereafter, the resulting solution was cooled to room temperature. 30 ml of toluene was added thereto to precipitate a solid material. The solid material was filtered off and dried under reduced pressure to obtain 0.30 g (yield of 18 mol %) of compound (I-c) which is a gray-brown powder.

$^1$H-NMR of compound (I-c) was as follows.

$^1$H-NMR: 3.38s (6H), 7.6-7.8m (2H), 8.33d (1H), 8.58d (1H), 8.71s (1H), 9.22d (2H)

Example 5

Synthesis of 4-(1-pyrrolidyl)-(5-trifluoromethyl-2-pyridyl) pyridinium chloride (I-d)

[Chemical formula 22]

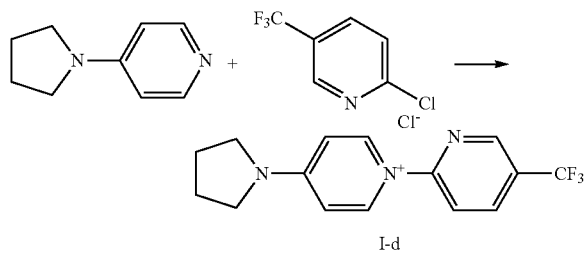

I-d 3.63 g (20 mmol) of 2-chloro-5-(trifluoromethyl) pyridine and 2.96 g (20 mmol) of 4-pyrrolidinopyridine were dissolved in 6 ml of N, N-dimethylformamide and heated at 120° C. for 4 hours. Thereafter, the resulting solution was ice-cooled and 6 ml of toluene was added thereto to precipitate a solid material. The solid material was collected by suction filtration. The solid material was washed with 5 ml of toluene and dried under reduced pressure to obtain 4.28 g (yield of 65 mol %) of compound (I-d) which is a pale brown powder.

Compound (I-d) had a melting point of 194-195° C. and $^1$H-NMR thereof was as follows.

$^1$H-NMR: 2.20 m (4H), 3.73 m (4H), 7.14 d (2H), 8.35 d (1H), 8.76 s (1H), 8.94 d (1H), 9.51 d (2H)

Example 6

Synthesis of 1-(3-trifluoromethyl-2-pyridyl)-4-(dimethylamino) pyridinium chloride (I-e)

[Chemical formula 23]

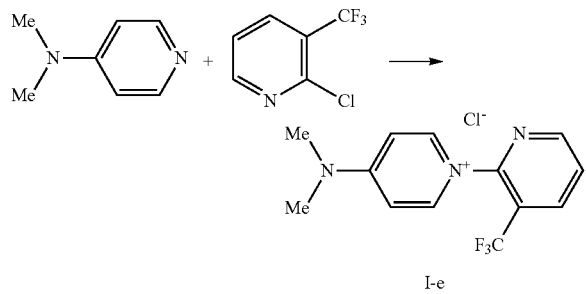

I-e 3.63 g (20 mmol) of 2-chloro-3-(trifluoromethyl) pyridine and 2.57 g (20 mmol) of 4-dimethylaminopyridine were dissolved in 10 ml of N, N-dimethylformamide and heated at 120° C. for 7 hours. Thereafter, the resulting solution was ice-cooled and 10 ml of toluene was added thereto to precipitate a solid material. The solid material was collected by suction filtration. The solid material was washed with 2 ml of toluene and dried under reduced pressure to obtain 4.19 g (yield of 69 mol %) of compound (I-e) which is a white powder.

Compound (I-e) had a melting point of 283-284° C. and $^1$H-NMR thereof was as follows.

$^1$H-NMR: 3.49 s (6H), 7.53 d (2H), 7.86 d (1H), 8.32-8.33 m (3H), 8.66 d (1H)

Example 7

Synthesis of 4-dimethylamino-1-(5-nitro-2-pyridyl) pyridinium chloride (Compound (I-f))

[Chemical formula 24]

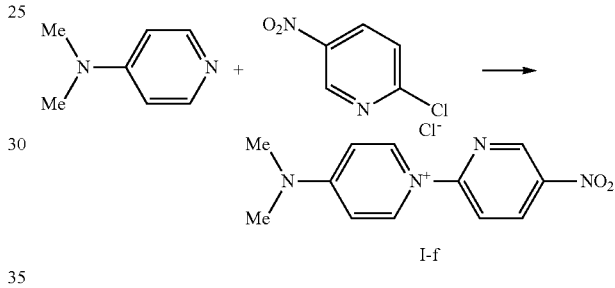

I-f 0.33 g (2 mmol) of 2-chloro-5-nitropyridine and 0.25 g (2 mmol) of 4-dimethylaminopyridine were dissolved in 1 ml of N, N-dimethylformamide and heated at 100° C. for 2 hours. Thereafter, the resulting solution was cooled to room temperature, and 1 ml of toluene was added thereto to precipitate a solid material. The obtained solid material was collected by suction filtration. The solid material was washed with 1 ml of toluene and dried under reduced pressure to obtain 0.56 g (yield of 100 mol %) of compound (I-f) which is a pale brown powder.

Compound (I-f) had a melting point of 217-218° C. and $^1$H-NMR thereof was as follows.

$^1$H-NMR (CD3OD): 3.41 s (6H), 7.25 d (2H), 8.18 d (1H), 8.90 d (1H), 8.99 d (2H), 9.42 s (1H)

Example 8

Synthesis of 1-(3-chloro-6-trifluoromethyl-2-pyridyl)-4-dimethylaminopyridinium chloride (Compound (I-g))

[Chemical formula 25]

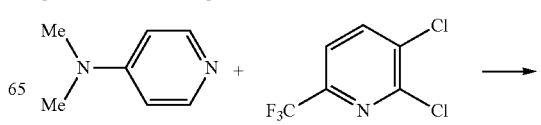

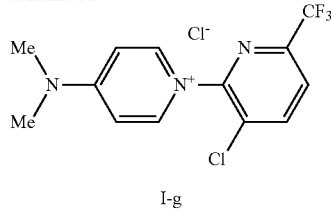

I-g 4.32 g (20 mmol) of 2,3-dichloro-6-(trifluoromethyl) pyridine and 2.44 g (2 mmol) of 4-dimethylaminopyridine were dissolved in 6 ml of N, N-dimethylformamide and heated at 120° C. for 3 hours. Thereafter, the resulting solution was ice-cooled and 6 ml of toluene was added thereto to precipitate a solid material. The solid material was collected by suction filtration. The obtained solid material was finely pulverized in a mortar, washed with 10 ml of ethyl acetate, and dried under reduced pressure to obtain 6.76 g (yield of 100 mol %) of compound (I-g) which is a pale brown powder.

compound (I-g) had a melting point of 141-143° C. and $^1$H-NMR thereof was as follows.

$^1$H-NMR: 3.48 s (6H), 7.52 d (2H), 8.21 s (1H), 8.67 d (2H), 8.78 s (1H)

Synthesis Example of Pyridine-2-yloxyamine Compound

Example 9

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 26]

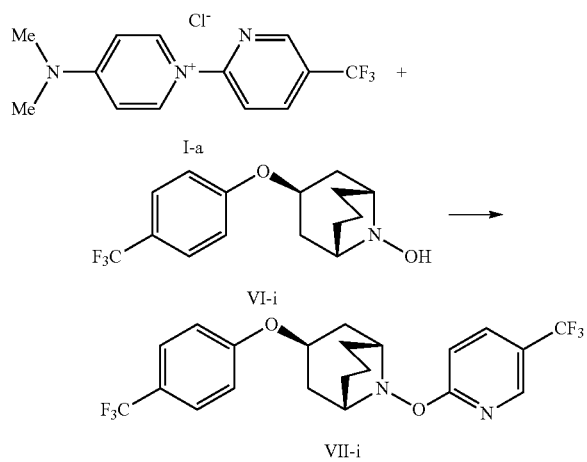

3.01 g (10 mmol) of 3-endo-(4-(trifluoromethyl) phenoxy)-9-hydroxy-9-azabicyclo [3,3,1] nonane (VI-i) and 4.56 g (15 mmol) of 1-(5-trifluoromethyl-2-pyridyl)-4-(dimethylamino) pyridinium chloride (I-a) were dissolved in 7 ml of tetrahydrofuran, and 1.72 g (13 mmol) of potassium t-butoxide dissolved in 13 ml of tetrahydrofuran was added thereto dropwise at 20° C. over 1 hour. The resulting mixture was further stirred at 20° C. for 2 hours. Thereafter, 10 ml of water and 2.03 g (19.5 mmol) of 35% hydrochloric acid were added to quench. The resulting mixture was extracted twice with 10 ml of toluene under acidic condition. The organic phase was dried over sodium sulfate. Thereafter, the resulting product was concentrated under reduced pressure. The obtained residue was purified by silica gel column chromatography (eluent, ethyl acetate:n-hexane=1:30) to obtain 4.27 g (yield of 95 mol %) of compound (VII-i) which is a white crystal.

Compound (VII-i) had a melting point of 94 to 95° C. and $^1$H-NMR thereof was as follows.

$^1$H-NMR: 1.2-1.5m (1H), 1.5-1.8m (4H), 2.0-2.5m (2H), 2.6-2.8m (2H), 3.5-3.7m (2H), 4.7-5.1 m (2H), 6.98-7.5d (1H), 7.2-7.5m (1H), 7.55d (2H), 7.89d (1H), 8.51s (1H)

Comparative Example 1

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 27]

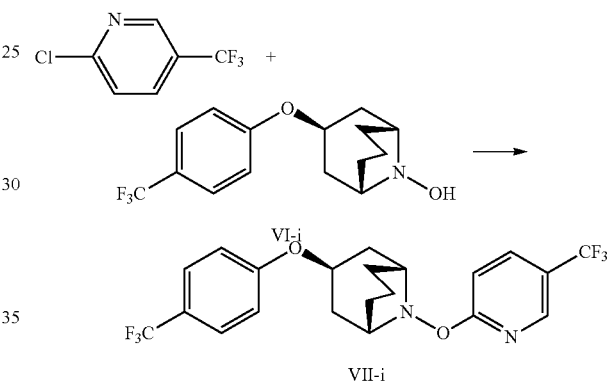

3.01 g (10 mmol) of 3-endo-(4-(trifluoromethyl) phenoxy)-9-hydroxy-9-azabicyclo [3,3,1] nonane (VI-i) and 2.81 g (15 mmol) of 2-chloro-5-(trifluoromethyl) pyridine were dissolved in 7 ml of tetrahydrofuran, and 1.72 g (13 mmol) of t-butoxy potassium dissolved in 13 ml of tetrahydrofuran was added thereto dropwise at −20° C. over 1 hour. The resulting mixture was further stirred at −20° C. for 3 hours. Thereafter, 20 ml of water was added to quench. The resulting mixture was extracted 3 times with 5 ml of toluene. The organic phase was dried over sodium sulfate. Thereafter, the resulting product was concentrated under reduced pressure. The obtained residue was purified by silica gel column chromatography (eluent, ethyl acetate:n-hexane=1:30 to 10) to obtain 3.99 g (yield of 90 mol %) of compound (VII-i) which is a white crystal.

Comparative Example 2

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 28]

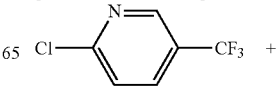

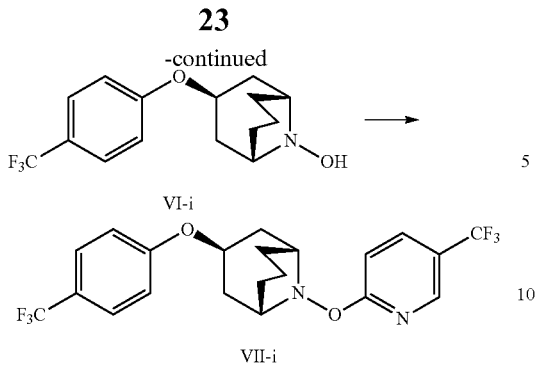

3.01 g (10 mmol) of 3-endo-(4-(trifluoromethyl) phenoxy)-9-hydroxy-9-hydroxy-9-azabicyclo [3,3,1] nonane (VI-i) and 2.81 g (15 mmol) of 2-chloro-5-(trifluoromethyl) pyridine were dissolved in 7 ml of tetrahydrofuran, and 1.72 g (13 mmol) of t-butoxy potassium dissolved in 13 ml of tetrahydrofuran was added thereto dropwise at 0° C. over 1 hour. The resulting mixture was further stirred at 0° C. for 3 hours. Thereafter, 20 ml of water was added to quench. The resulting product was extracted 3 times with 5 ml of toluene. The organic phase was dried over sodium sulfate. Thereafter, the resulting product was concentrated under reduced pressure. The obtained residue was purified by silica gel column chromatography (eluent, ethyl acetate:n-hexane=1:30 to 10) to obtain 3.87 g (yield of 87 mol %) of compound (VII-i) which is a white crystal.

Comparative Example 3

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 29]

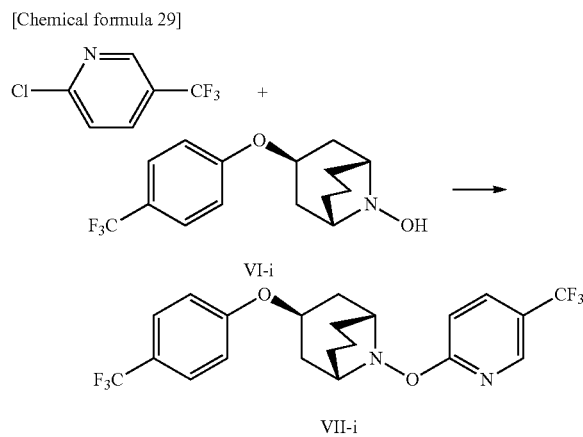

3.01 g (10 mmol) of 3-endo-(4-(trifluoromethyl) phenoxy)-9-hydroxy-9-azabicyclo [3,3,1] nonane (VI-i) and 2.81 g (15 mmol) of 2-chloro-5-(trifluoromethyl) pyridine were dissolved in 7 ml of tetrahydrofuran, and 1.72 g (13 mmol) of t-butoxy potassium dissolved in 13 ml of tetrahydrofuran was added thereto dropwise at 20° C. over 1 hour. The resulting mixture was further stirred at 20° C. for 2 hours. Thereafter, 20 ml of water was added to quench. The resulting mixture was extracted 3 times with 5 ml of toluene. The organic phase was dried over sodium sulfate. Thereafter, the resulting product was concentrated under reduced pressure. The obtained residue was purified by silica gel column chromatography (eluent, ethyl acetate:n-hexane=1:30 to 10) to obtain 3.26 g (yield of 73 mol %) of compound (VII-i) which is a white crystal.

Example 10

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 30]

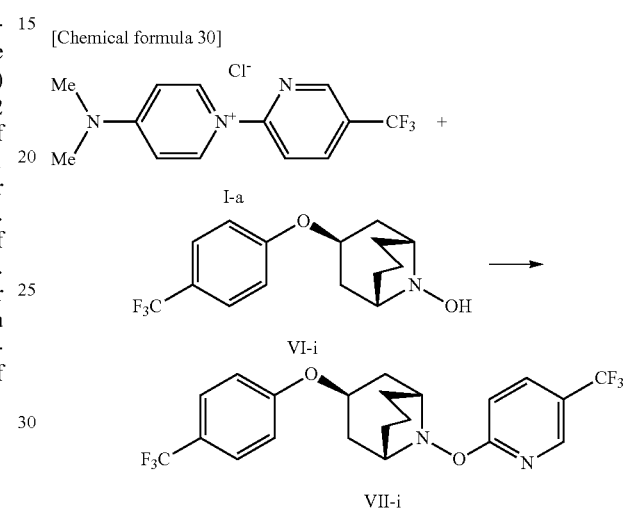

3.01 g (10 mmol) of 3-endo-(4-(trifluoromethyl) phenoxy)-9-hydroxy-9-azabicyclo [3,3,1] nonane (VI-i) and 3.95 g (13 mmol) of 1-(5-trifluoromethyl-2-pyridyl)-N,N-dimethyl-4-amino-pyridinium chloride (I-a) were dissolved in 11 ml of N, N-dimethylformamide, and 0.87 g (15 mmol) of potassium hydroxide powder and 0.18 g (10 mmol) of water were added thereto. The resulting mixture was stirred at 30° C. for 4.5 hours. Then, 0.29 g (5 mmol) of potassium hydroxide powder was added, and stirred at 30° C. for 2 hours. Thereafter, 20 ml of water was added to quench. The resulting mixture was extracted 3 times with 10 ml of toluene. The organic phase was dried over sodium sulfate. The obtained organic phase was analyzed by HPLC using octanophenone as an internal standard. The organic phase contained 4.15 g (yield of 93 mol %) of compound (VII-i).

Comparative Example 4

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 31]

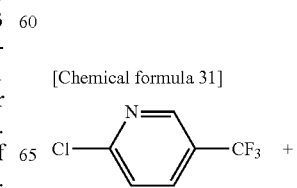

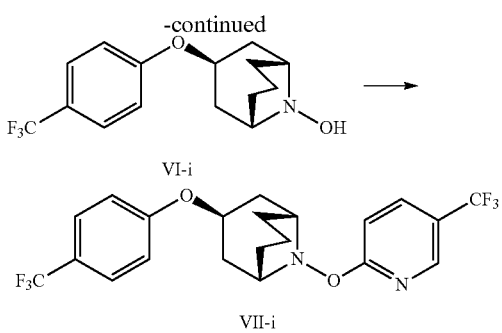

3.01 g (10 mmol) of 3-endo-(4-(trifluoromethyl) phenoxy)-9-hydroxy-9-azabicyclo [3,3,1] nonane (VI-i) and 3.95 g (13 mmol) of 2-chloro-5-(trifluoromethyl) pyridine were dissolved in 11 ml of N, N-dimethylformamide, and 0.87 g (15 mmol) of potassium hydroxide powder and 0.18 g (10 mmol) of water were added thereto at 30° C. Thereafter, the resulting mixture was stirred at 30° C. for 4.5 hours. 0.29 g (5 mmol) of potassium hydroxide powder was added thereto, and the resulting mixture was stirred at 30° C. for 2 hours. Thereafter, 20 ml of water was added to quench. The resulting mixture was extracted 3 times with 10 ml of toluene. The organic phase was dried over sodium sulfate. The obtained organic phase was analyzed by HPLC using octanophenone as an internal standard. The organic phase contained 2.36 g (yield of 53 mol %) of compound (VII-i).

Example 11

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 32]

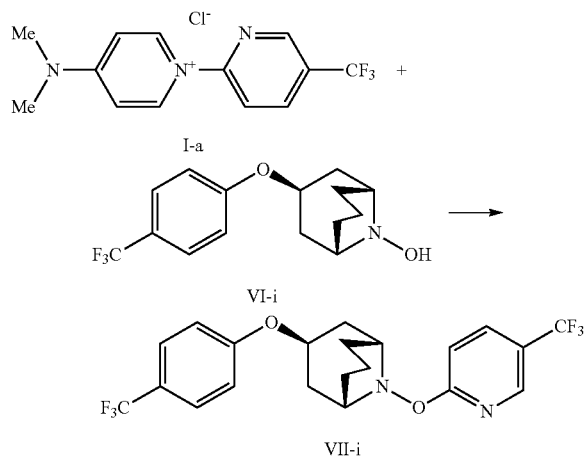

3.01 g (10 mmol) of 3-endo-(4-(trifluoromethyl) phenoxy)-9-hydroxy-9-azabicyclo [3,3,1] nonane (VI-i) and 3.95 g (13 mmol) of 1-(5-trifluoromethyl-2-pyridyl)-N,N-dimethyl-4-amino-pyridinium chloride (I-a) were dissolved in 11 ml of N, N-dimethylformamide and 1.07 g (15 mmol) of ethoxy sodium was dividedly added thereto in 12 times at 10° C. over 1 hour. Thereafter, the resulting mixture was stirred at 10° C. for 1 hour. 20 ml of water was added thereto to quench. The resulting mixture was extracted 3 times with 10 ml of toluene. The organic phase was dried over sodium sulfate. The obtained organic phase was analyzed by HPLC using octanophenone as an internal standard. The organic phase contained 3.88 g (yield of 87 mol %) of compound (VII-i).

Example 12

Synthesis of 3-endo-(4-(trifluoromethyl) phenoxy)-9-(5-(trifluoromethyl)-2-pyridyloxy)-9-azabicyclo [3,3,1] nonane (Compound (VII-i))

[Chemical formula 33]

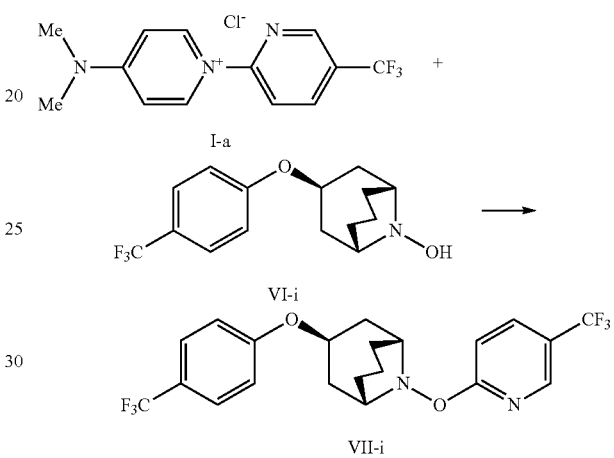

3.01 g (10 mmol) of 3-endo-(4-(trifluoromethyl) phenoxy)-9-hydroxy-9-azabicyclo [3,3,1] nonane (VI-i) and 3.95 g (13 mmol) of 1-(5-trifluoromethyl-2-pyridyl)-N, N-dimethyl-4-amino-pyridinium chloride (I-a) were dissolved in 11 ml of N, N-dimethylformamide, and 13 mmol of sodium hydride was dividedly added thereto at 0° C. over 2 hours. Thereafter, the resulting mixture was stirred at 20° C. for 1 hour. 20 ml of water was added thereto to quench. The resulting mixture was extracted 3 times with 10 ml of toluene. The organic phase was dried over sodium sulfate. The obtained organic phase was analyzed by HPLC using octanophenone as an internal standard. The organic phase contained 3.88 g (yield of 87 mol %) of compound (VII-i).

Example 13

Synthesis of 3-endo-(2-isobutoxy-4-(trifluoromethyl) phenoxy)-9-(5-(trifluoromethyl)-2-pyridyloxy)-9-azabicyclo [3,3,1] nonane (Compound (VII-ii))

[Chemical formula 34]

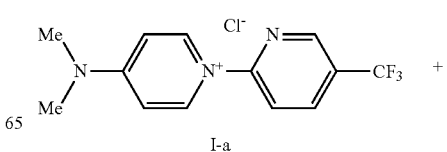

-continued

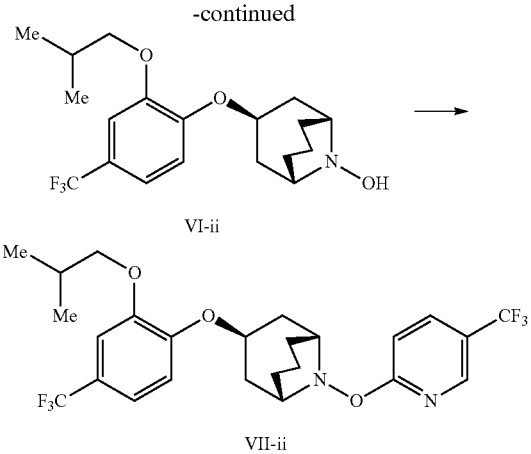

1.50 g (4 mmol) of compound (VI-ii) and 1.58 g (5.2 mmol) of compound (I-a) were dissolved in 4 ml of N,N-dimethylformamide, and 0.336 g (6 mmol) of potassium hydroxide powder and 72 mg (4 mmol) of water were added thereto at room temperature. The resulting mixture was stirred at 30-35° C. for 6 hours. 30 ml of cold water was added thereto to quench. The resulting product was extracted twice with 20 ml of toluene. The organic phase was washed twice with 10 ml of water and washed once with 10 ml of saturated brine. After that, the resulting product was dried with MgSO$_4$ and concentrated under reduced pressure. The obtained residue was purified by silica gel column chromatography (eluent, ethyl acetate:n-hexane=1:10) to obtain 1.78 g (yield of 86 mol %) of compound (VII-ii) which is a white crystal.

Compound (VII-ii) had a melting point of 80 to 82° C. and $^1$H-NMR thereof was as follows.

$^1$H-NMR: 1.08d (6H), 1.2-3.8m (11H), 3.5-3.6m (2H), 3.7-4.2m (2H), 4.6-4.9m (1H), 6.8-7.5m (4H), 7.8-7.9m (1H), 8.49s (1H)

Example 14

Synthesis of 3-endo-(2-isobutoxy-4-(trifluoromethyl) phenoxy)-9-(5-(trifluoromethyl)-2-pyridyloxy)-9-azabicyclo [3,3,1] nonane (Compound (VII-ii))

[Chemical formula 35]

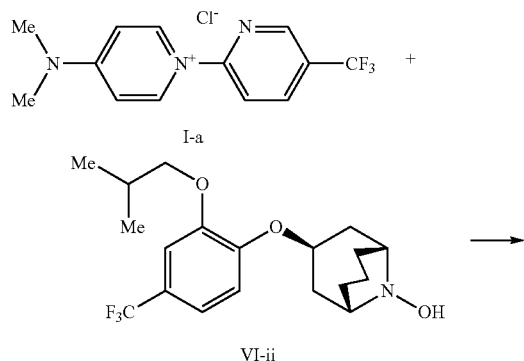

-continued

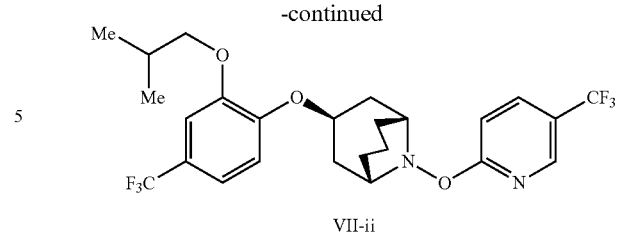

1.50 g (4 mmol) of compound (VI-ii) and 1.58 g (5.2 mmol) of compound (I-a) were dissolved in 4 ml of N,N-dimethylformamide, and 0.336 g (6 mmol) of potassium hydroxide powder and 72 mg (4 mmol) of water were added thereto at room temperature. The resulting mixture was stirred at 30-35° C. for 6 hours. Thereafter, 30 ml of cold water was added to quench. The resulting product was extracted twice with 20 ml of toluene. The organic phase was washed twice with 10 ml of water and washed once with 10 ml of saturated brine. After that, the resulting product was dried with MgSO$_4$ and concentrated under reduced pressure. The obtained residue was purified by silica gel column chromatography (eluent, ethyl acetate:n-hexane=1:10) to obtain 1.80 g (yield of 87 mol %) of compound (VII-ii) which is a white crystal.

Comparative Example 5

Synthesis of 3-endo-(2-isobutoxy-4-(trifluoromethyl) phenoxy)-9-(5-(trifluoromethyl)-2-pyridyloxy)-9-azabicyclo [3,3,1] nonane (Compound (VII-ii))

[Chemical formula 36]

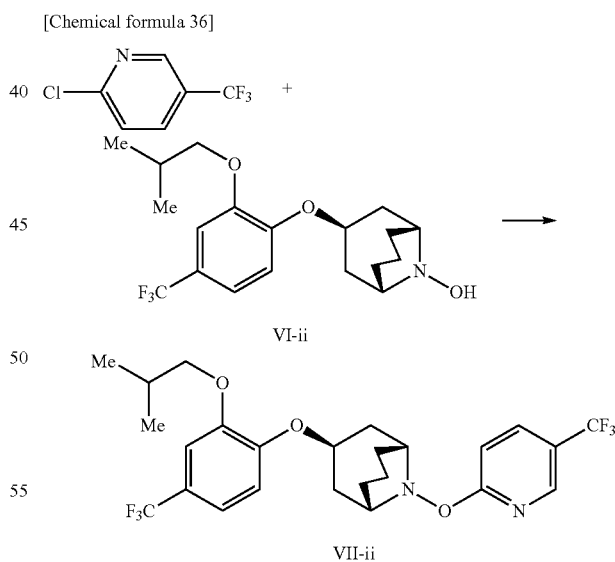

1.50 g (4 mmol) of compound (VI-ii) and 0.944 g (5.2 mmol) of 2-chloro-5-(trifluoromethyl) pyridine were dissolved in 4 ml of N, N-dimethylformamide, and 0.336 g (6 mmol) of potassium hydroxide powder and 72 mg (4 mmol) of water were added thereto at room temperature. The resulting mixture was stirred at 30-35° C. for 6 hours. Thereafter, 30 ml of cold water was added to quench. The resulting product was extracted twice with 20 ml of toluene.

The organic phase was washed twice with 10 ml of water and washed once with 10 ml of saturated brine. The resulting product was then dried over MgSO$_4$ and concentrated under reduced pressure. The obtained residue was purified by silica gel column chromatography (eluent, ethyl acetate:n-hexane=1:10) to obtain 1.036 g (yield of 50 mol %) of compound (VII-ii) which is a white crystal.

Example 15

Synthesis of 3-endo-(2-methoxymethoxy-4-(trifluoromethyl) phenoxy)-9-(5-(trifluoromethyl)-2-pyridyloxy)-9-azabicyclo [3,3,1] nonane (Compound (VII-iii))

[Chemical formula 37]

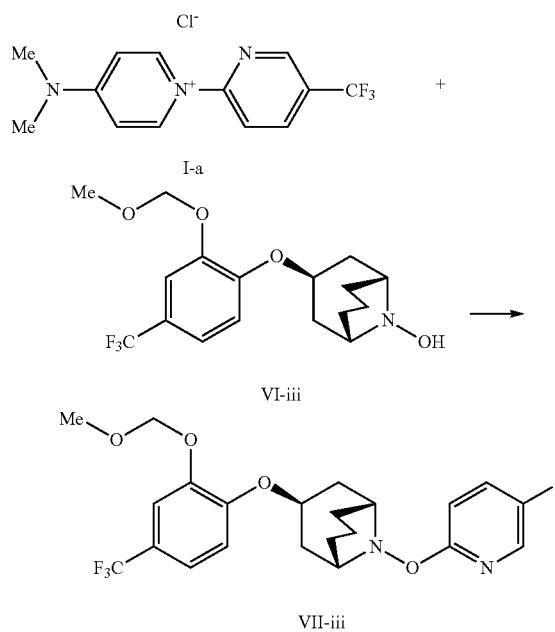

2.14 g (5.92 mmol) of compound (VI-iii) and 2.41 g (7.93 mmol) of compound (I-a) were dissolved in 6 ml of N, N-dimethylformamide, and 0.503 g (8.96 mmol) of potassium hydroxide powder and 90 mg (5.0 mmol) of water were added thereto at room temperature. The resulting mixture was stirred at 30 to 32° C. for 6 hours. Thereafter, 50 ml of cold water was added to quench. The resulting product was extracted 3 times with 30 ml of ethyl acetate. The organic phase was washed 3 times with 20 ml of water and washed once with 20 ml of saturated brine. The resulting product was then dried over MgSO$_4$ and concentrated under reduced pressure. The obtained residue was purified by silica gel column chromatography (eluent, ethyl acetate:n-hexane=1: 15 to 9) to obtain 2.71 g (yield of 90 mol %) of compound (VII-iii) which is a white crystal.

Compound (VII-iii) had a melting point of 52 to 55° C. and $^1$H-NMR thereof was as follows.

$^1$H-NMR: 1.2-1.8m (5H), 2.0-2.2m (2H), 2.4-2.8m (3H), 3.53s (3H), 3.6-3.8brs (2H), 4.7-5.1m (1H), 5.22s (2H), 6.99t (1H), 7.26d (1H), 7.38t (2H), 7.89d (1H), 8.50s (1H)

Example 16

Synthesis of 3-endo-(2-methoxymethoxy-4-(trifluoromethyl) phenoxy)-9-(5-(trifluoromethyl)-2-pyridyloxy)-9-azabicyclo [3,3,1] nonane (Compound (VII-iii))

[Chemical formula 38]

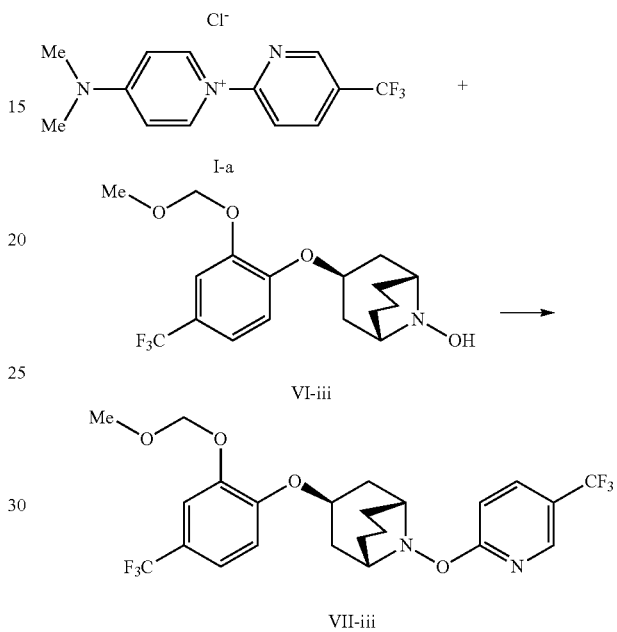

2.033 g (5.62 mmol) of compound (VI-iii) and 2.439 g (8.03 mmol) of compound (I-a) were dissolved in 5.6 ml of N, N-dimethylformamide, and 0.473 g (8.43 mmol) of potassium hydroxide powder and 101 mg (5.61 mmol) of water were added at room temperature. The resulting mixture was stirred at 33-35° C. for 16 hours. Thereafter, 20 ml of cold water was added to quench. The resulting product was extracted 3 times with 20 ml of ethyl acetate. The organic phase was washed 3 times with 15 ml of water and washed once with 10 ml of saturated brine. The resulting product was then dried over MgSO$_4$ and then concentrated. The obtained organic phase was analyzed by HPLC using octanophenone as an internal standard. The organic phase contained 2.73 g (yield of 96 mol %) of compound (VII-iii).

Comparative Example 6

Synthesis of 3-endo-(2-methoxymethoxy-4-(trifluoromethyl) phenoxy)-9-(5-(trifluoromethyl)-2-pyridyloxy)-9-azabicyclo [3,3,1] nonane (Compound (VII-iii))

[Chemical formula 39]

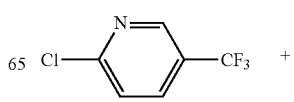

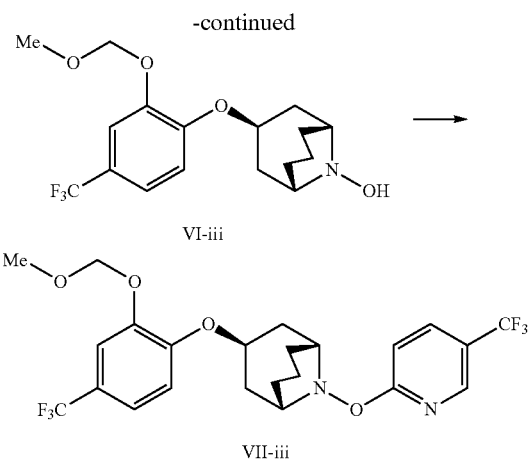

2.044 g (5.56 mmol) of compound (VI-iii) and 1.471 g (8.10 mmol) of 2-chloro-5-(trifluoromethyl) pyridine were dissolved in 5.6 ml of N. N-dimethylformamide, and 0.472 g (8.41 mmol) of potassium hydroxide powder and 101 mg (5.61 mmol) of water were added thereto at room temperature. The resulting mixture was stirred at 34-35° C. for 17 hours. Thereafter, 20 ml of cold water was added to quench. The resulting product was extracted 3 times with 20 ml of ethyl acetate. The organic phase was washed 3 times with 15 ml of water and washed once with 10 ml of saturated brine. The resulting material was then dried over $MgSO_4$ and then concentrated. The obtained organic phase was analyzed by HPLC using octanophenone as an internal standard. The organic phase contained 1.26 g (yield of 44 mol %) of compound (VII-iii).

Example 17

[Chemical formula 40]

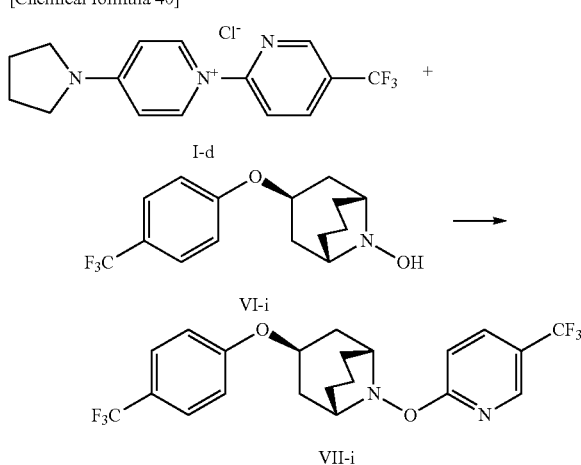

3.01 g (10 mmol) of 3-endo-(4-(trifluoromethyl) phenoxy)-9-hydroxy-9-azabicyclo [3,3,1] nonane (VI-i) and 4.29 g (13 mmol) of 4-(1-pyrrolidyl)-(5-trifluoromethyl-2-pyridyl) pyridinium chloride (I-d) were dissolved in 11 ml of N, N-dimethylformamide, and 0.87 g (15 mmol) of potassium hydroxide powder and 0.18 g (10 mmol) of water were added thereto at 30° C., followed by stirring at 30° C. for 3 hours. Then. 0.58 g (10 mmol) of potassium hydroxide powder was added, followed by stirring at 30° C. for 2 hours. Thereafter, 20 ml of cold water was added to quench. The resulting product was extracted 3 times with 10 ml of toluene. The obtained organic phase was dried over sodium sulfate. The organic phase was analyzed by HPLC using octanophenone as internal standard. The organic phase contained 4.19 g (yield of 94 mol %) of compound (VII-i).

Example 18

Synthesis of 3-endo-(4-(trifluoromethyl) phenoxy)-9-(3-(trifluoromethyl)-2-pyridyloxy)-9-azabicyclo [3,3,3] nonane (Compound (VII-iv))

[Chemical formula 41]

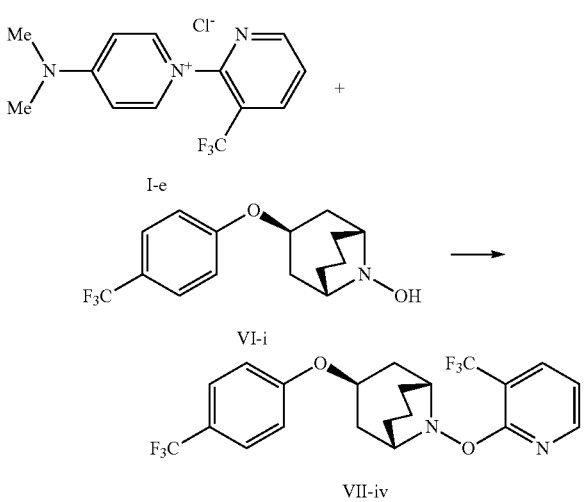

3.01 g (10 mmol) of 3-endo-(4-(trifluoromethyl) phenoxy)-9-hydroxy-9-azabicyclo [3,3,1] nonane (VI-i) and 3.95 g (13 mmol) of 1-(3-trifluoromethyl-2-pyridyl)-4-(dimethylamino) pyridinium chloride (I-e) were dissolved in 11 ml of N, N-dimethylformamide, and 0.87 g (15 mmol) of potassium hydroxide powder and 0.18 g (10 mmol) of water were added thereto at 30° C., followed by stirring at 30° C. for 4 hours. Thereafter, 20 ml of water was added to quench. The resulting product was extracted 3 times with 10 ml of toluene. The organic phase was dried over $MgSO_4$ and concentrated under reduced pressure. The resulting residue was purified by silica gel column chromatography (eluent, ethyl acetate:n-hexane=1:30 to 10) to obtain 4.22 g (yield 95 mol %) of compound (VII-iv) which is pale yellow and oily.

$^1$H-NMR of compound (VII-iv) was as follows.

$^1$H-NMR ($CDCl_3$, 400 MHz): 1.32-1.44 m (1H), 1.62-1.73 m (4H), 2.01-2.37 m (3H), 2.60-2.84 m (2H), 5.08 m (1H), 6.97-7.02 m (3H), 7.55 d (2H), 7.88 d (1H), 8.44 d (1H)

$^1$H-NMR Measurement Conditions (Unless Otherwise Stated):

400 MHz. Solvent $CDCl_3$, Internal standard TMS=0 ppm HPLC Analysis Conditions:

Column: Inertsil ODS-4 (5 μm, 4.6 mm×150 mm), Mobile phase: $CH_3CN/H_2O$/10% phosphoric acid=800/200/1 (v/v/v), Wavelength: 235 nm, Flow rate: 1.0 ml/min, Column temperature: 40° C., Standard sample: n-octanophenone

Example 19

Synthesis of 3-endo-(2-cyano-4-methoxyphenoxy)-9-(5-(trifluoromethyl)-2-pyridyloxy)-9-azabicyclo [3,3,1] nonane (Compound (VII-iv))

[Chemical formula 42]

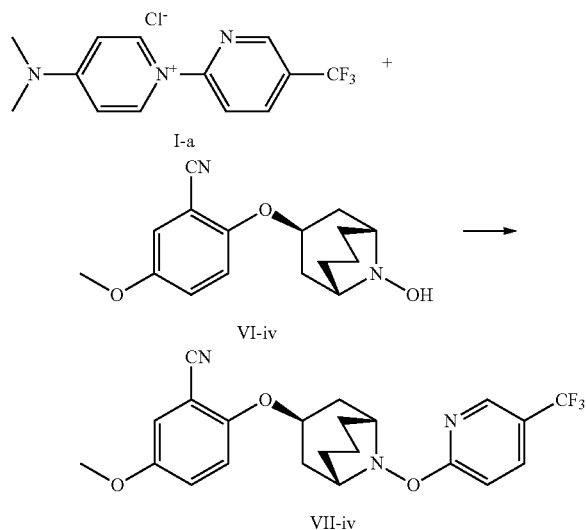

0.80 g (2.8 mmol) of 3-endo-(2-cyano-4-methoxyphenoxy)-9-hydroxy-9-azabicyclo [3,3,1] nonane (VI-iv) and 1.09 g (3.6 mmol) of 1-(5-trifluoromethyl-2-pyridyl)-4-dimethylaminopyridinium chloride (I-a) were dissolved in 3 mL of N, N-dimethylformamide, and 0.23 g (4.1 mmol) of potassium hydroxide powder and 50 mg (2.8 mmol) of water were added thereto at 35° C. The resulting mixture was stirred at 30 to 35° C. for 17 hours. 30 mL of water was added thereto to quench. The resulting product was extracted twice with 30 mL of ethyl acetate. The organic layer was washed once with 20 mL of saturated brine. The resulting product was then dried over magnesium sulfate and concentrated under reduced pressure. The obtained residue was purified by silica gel column chromatography (Yamazen column) to obtain 1.01 g (yield of 83%) of compound (VII-iv). mp 131-134° C. (white crystal)

$^1$H-NMR (CDCl$_3$, δ ppm) 1.35-2.74 (m, 10H), 3.59-3.61 (m, 2H), 3.78 (s, 3H), 4.64-5.00 (m, 1H), 6.91-6.95 (m, 1H), 7.04-7.10 (m, 2H), 7.38-7.40 (d, 1H), 7.84-7.89 (d, 1H), 8.48 (s, 1H)

Example 20

Synthesis of 3-endo-methoxy-9-(5-(trifluoromethyl)-2-pyridyloxy)-9-azabicyclo [3,3,1] nonane (Compound (VII-v))

[Chemical formula 43]

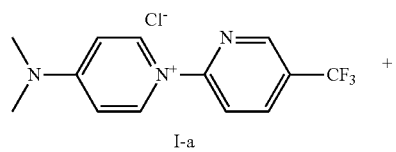

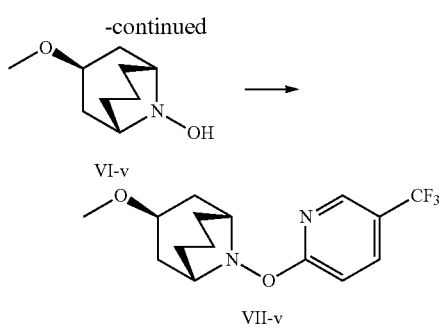

0.34 g (2.0 mmol) of 3-endo-methoxy-9-hydroxy-9-azabicyclo [3,3,1] nonane (VI-v) and 0.79 g (2.6 mmol) of 1-(5-trifluoromethyl-2-pyridyl)-4-dimethylaminopyridinium chloride (I-a) were dissolved in 2 mL of N, N-dimethylformamide, and 0.17 g (3.0 mmol) of potassium hydroxide powder and 35 mg (1.94 mmol) of water were added thereto at 35° C. The resulting mixture was stirred at 30-35° C. for 18 hours. 20 mL of water was added thereto to quench. The resulting product was extracted twice with 30 mL of ethyl acetate. The organic layer was washed once with 20 mL of saturated brine. The resulting product was then dried over magnesium sulfate and concentrated under reduced pressure. The obtained residue was purified by silica gel column chromatography (Yamazen column) to obtain 0.52 g (yield: 87%) of compound (VII-v). mp 58-59° C. (white crystal)

$^1$H-NMR (CDCl$_3$, δ ppm) 1.22-2.56 (m, 10H), 3.36 (s, 3H), 3.50-3.57 (m, 2H), 3.61-4.00 (m, 1H), 7.34-7.36 (d, 1H), 7.83-7.87 (d, 1H), 8.46 (s, 1H)

Example 21

Synthesis of 3-endo-allyloxy-9-(5-(trifluoromethyl)-2-pyridyloxy)-9-azabicyclo [3,3,1] nonane (Compound (VII-vi))

[Chemical formula 44]

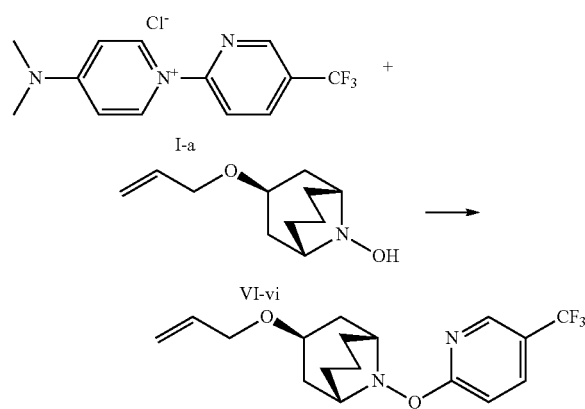

0.35 g (1.8 mmol) of 3-endo-allyloxy-9-hydroxy-9-azabicyclo [3,3,1] nonane (VI-vi) and 0.70 g (2.3 mmol) of 1-(5-trifluoromethyl-2-pyridyl)-4-dimethylaminopyridinium chloride (I-a) were dissolved in 2 mL of N, N-dimethylformamide, and 0.15 g (2.7 mmol) of potassium hydroxide powder and 30 mg (1.7 mmol) of water were added at 35° C. The resulting mixture was stirred at 30 to 35° C. for 17 hours. 20 mL of water was added thereto to quench. The resulting product was extracted twice with 30 mL of ethyl acetate. The organic layer was washed once with 20 mL of saturated brine. The resulting product was then dried over magnesium sulfate and concentrated under reduced pressure. The resulting residue was purified by silica gel column chromatography (Yamazen column) to obtain 0.54 g (yield of 86%) of compound (VII-vi).

$n_D^{20.3}$ 1.4888 (colorless transparent oily matter)

$^1$H-NMR (CDCl$_3$, δ ppm) 1.22-2.57 (m, 10H), 3.50-3.57 (m, 2H), 3.78-4.16 (m, 3H), 5.13-5.32 (m, 2H), 5.88-5.99 (m, 1H), 7.22-7.36 (d, 1H), 7.83-7.86 (d, 1H), 8.46 (s, 1H)

Example 22

Synthesis of 3-endo-pivalate-9-(5-(trifluoromethyl)-2-pyridyloxy)-9-azabicyclo [3,3,1] nonane (Compound (VII-vi))

[Chemical formula 45]

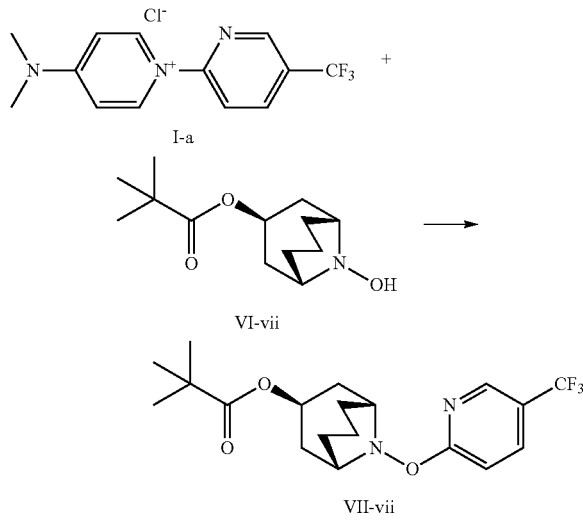

0.55 g (2.3 mmol) of 3-endo-t-butylcarbonyloxy-9-hydroxy-9-azabicyclo [3,3,1] nonane (VI-vi) and 0.91 g (3.0 mmol) of 1-(5-trifluoromethyl-2-pyridyl)-4-dimethylaminopyridinium chloride (I-a) were dissolved in 3 mL of N,N-dimethylformamide, and 0.19 g (3.4 mmol) of potassium hydroxide powder and 40 mg (2.3 mmol) of water were added thereto at 35° C. The resulting mixture was stirred at 30-35° C. for 6 hours. 20 mL of water was added thereto to quench. The resulting product was extracted twice with 30 mL of ethyl acetate. The organic layer was washed once with 20 mL of saturated brine. The resulting product was then dried over magnesium sulfate and concentrated under reduced pressure. The obtained residue was purified by silica gel column chromatography (Yamazen column) to obtain 0.70 g (yield 78%) of compound (VII-vi). mp 89-91° C. (white crystal)

$^1$H-NMR (CDCl$_3$, δ ppm) 1.20 (s, 9H), 1.24-2.69 (m, 10H), 3.50-3.55 (m, 2H), 5.11-5.36 (m, 1H), 7.25-7.32 (d, 1H), 7.83-7.86 (d, 1H), 8.46 (s, 1H)

INDUSTRIAL APPLICABILITY

A pyridine-2-ylpyridinium compound useful for producing a pyridine-2-yloxyamine compound having excellent acaricidal activity and excellent safety with a high yield by stably reacting at a temperature around room temperature can be provided.

The invention claimed is:

1. A compound represented by formula (I),

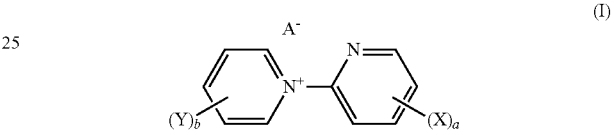

in formula (I), A$^-$ represents a halogen ion, an unsubstituted or substituted benzenesulfonate ion, or an unsubstituted or substituted C1-C8 alkylsulfonate ion (excluding trifluoromethane sulfonate ion), X is $C_nZ_pF_{2n+1-p}$, a is an integer of 1 to 4, and when a is 2 or more, $C_nZ_pF_{2n+1-p}$ may be the same or different, n is an integer from 1 to 6, p is an integer from 0 to 9, Z represents a hydrogen atom or a halogen atom, Y is a group represented by NR$^1$R$^2$ substituting at the 4-position, b is 1, R$^1$ and R$^2$ each independently represent an unsubstituted or substituted C1-C8 alkyl group, and R$^1$ and R$^2$ may bond together to form a ring containing a nitrogen atom to which they are bonded as a constituting atom of the ring.

2. The compound according to claim 1, wherein A$^-$ is a chlorine ion, and R$^1$ and R$^2$ are methyl groups.

3. The compound according to claim 1, wherein a is 1, and X is CF$_3$ substituting at the 5-position.

* * * * *